(12) United States Patent
Brink et al.

(10) Patent No.: US 8,318,637 B2
(45) Date of Patent: Nov. 27, 2012

(54) HERBICIDE/AZOLE COMBINATION

(75) Inventors: Arne Brink, Langenfeld (DE); Rolf Pontzen, Leichlingen (DE); Stefan Dutzmann, Langenfeld (DE)

(73) Assignee: Bayer Cropscience AG, Monheim (DE)

( * ) Notice: Subject to any disclaimer, the term of this patent is extended or adjusted under 35 U.S.C. 154(b) by 98 days.

(21) Appl. No.: 12/743,738

(22) PCT Filed: Nov. 15, 2008

(86) PCT No.: PCT/EP2008/009681
§ 371 (c)(1), (2), (4) Date: May 19, 2010

(87) PCT Pub. No.: WO2009/068193
PCT Pub. Date: Jun. 4, 2009

(65) Prior Publication Data
US 2010/0255995 A1    Oct. 7, 2010

(30) Foreign Application Priority Data
Nov. 29, 2007  (EP) .................................. 07023140

(51) Int. Cl.
*A01N 43/64* (2006.01)
(52) U.S. Cl. ..................................................... 504/134
(58) Field of Classification Search ........................ None
See application file for complete search history.

(56) References Cited

U.S. PATENT DOCUMENTS

2007/0010399 A1*  1/2007  Rosinger et al. .............. 504/111

FOREIGN PATENT DOCUMENTS

| EP | 0 182 740 | 5/1986 |
|---|---|---|
| EP | 0 612 473 | 8/1994 |
| WO | 96/19110 | 6/1996 |
| WO | 98/35560 | 8/1998 |
| WO | 99/65314 | 12/1999 |
| WO | 02/054867 | 7/2002 |
| WO | 03/043422 | 5/2003 |
| WO | 03/051122 | 6/2003 |
| WO | 2004/004463 | 1/2004 |
| WO | 2004/008849 | 1/2004 |

OTHER PUBLICATIONS

International Search Report of PCT/EP2008/009681, dated Feb. 15, 2010 (6 pages).

* cited by examiner

*Primary Examiner* — Alton Pryor
(74) *Attorney, Agent, or Firm* — Baker Donelson Bearman Caldwell & Berkowitz PC

(57) ABSTRACT

Herbicide/azole combination comprising components (A) and (B) having improved effects, where
(A) is one or more herbicidally active compounds from the group of the ALS inhibitors, and
(B) is one or more agrochemically active azole compounds, preferably from the group of the triazoles, pyrazoles and triazolinethiones.

20 Claims, No Drawings

HERBICIDE/AZOLE COMBINATION

CROSS REFERENCE TO RELATED APPLICATIONS

This application is a §371 National Stage Application of PCT/EP2008/009681 filed Nov. 15, 2008, which claims priority to European Application 07023140.2 filed Nov. 29, 2007.

BACKGROUND OF THE INVENTION

1. Field of the Invention

The invention is in the technical field of the crop protection agents which can be used against harmful plants, for example in crop plants, and relates to a combination of specific herbicides with agrochemically active azole compounds.

2. Description of Related Art

The publication WO 92/11761 discloses compositions comprising a herbicide a) and a biocide b) and also an antidote c) which counteracts the increased phytotoxic action of the herbicide a) due to biocide b).

SUMMARY OF THE INVENTION

It was an object of the present invention to provide an improved herbicidally active active compound combination.

Surprisingly, it has now been found that herbicides from the group of the ALS inhibitors in combination with agrochemically active compounds from the group of the azoles act together in a particularly favorable manner and show, for example, synergistic effects.

Accordingly, the present invention provides a herbicide/azole combination comprising components (A) and (B), where A) is one or more herbicidally active compounds from the group of the ALS inhibitors, and
B) is one or more agrochemically active azole compounds, preferably from the group of the triazoles, pyrazoles and triazolinethiones.

DETAILED DESCRIPTION OF A PREFERRED EMBODIMENT

Suitable ALS inhibitors A) are, for example, compounds from the group of the imidazolinones, pyrimidinyloxypyridinecarboxylic acid derivatives, pyrimidyloxy-benzoic acid derivatives or the sulfonamides, such as triazolopyrimidinesulfonamides, sulfonylaminocarbonyltriazolinones or sulfonylureas. Preference is given to sulfonamides, for example phenylsulfonamides, heteroarylsulfonamides and sulfonediamides (for example cyclosulfamuron or (alkylsulfonyl)alkylaminosulfonamides such as amidosulfuron).

Suitable phenylsulfonamides A) are, for example, compounds from the group of the phenylsulfonylaminocarbonyltriazolinones or the phenylsulfonylureas, preferably from the group of the phenylsulfonylureas. The term phenylsulfonylureas is to be understood as including those sulfonylureas in which the phenyl group is attached to the sulfone group ($SO_2$) via a spacer such as $CH_2$, O or NH. Examples of phenylsulfonylaminocarbonyltriazolinones are flucarbazone and propoxycarbazone and their salts. The ALS inhibitors A) are commercially available and/or can be prepared by known processes as described, for example, in EP-A-7687, EP-A-30138, U.S. Pat. Nos. 5,057,144 and 5,534,486.

Suitable phenylsulfonamides are, for example, phenylsulfonamides of the formula (I) and/or their salts

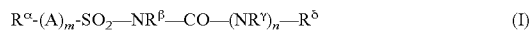  (I)

in which
$R^\alpha$ is an unsubstituted or substituted phenyl radical, where the phenyl radical including substituents has 1-30 carbon atoms, preferably 1-20 carbon atoms,
$R^\beta$ is a hydrogen atom or an unsubstituted or substituted hydrocarbon radical which, including substituents, has 1-10 carbon atoms, for example unsubstituted or substituted $C_1$-$C_6$ alkyl, preferably a hydrogen atom or methyl,
$R^\gamma$ is a hydrogen atom or an unsubstituted or substituted hydrocarbon radical which, including substituents, has 1-10 carbon atoms, for example unsubstituted or substituted $C_1$-$C_6$ alkyl, preferably a hydrogen atom or methyl,
A is $CH_2$, O or NH, preferably O,
m is zero or 1,
n is zero or 1, preferably 1, and
$R^\delta$ is a heterocyclic radical such as a pyrimidinyl radical, a triazinyl radical or a triazolinone radical.

Preferred phenylsulfonamides are phenylsulfonylureas, for example phenylsulfonylureas of the formula (II) and/or their salts

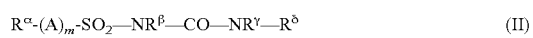  (II)

in which
$R^\alpha$ is an unsubstituted or substituted phenyl radical, where the phenyl radical including substituents has 1-30 carbon atoms, preferably 1-20 carbon atoms,
$R^\beta$ is a hydrogen atom or an unsubstituted or substituted hydrocarbon radical which, including substituents, has 1-10 carbon atoms, for example unsubstituted or substituted $C_1$-$C_6$ alkyl, preferably a hydrogen atom or methyl,
$R^\gamma$ is a hydrogen atom or an unsubstituted or substituted hydrocarbon radical which, including substituents, has 1-10 carbon atoms, for example unsubstituted or substituted $C_1$-$C_6$ alkyl, preferably a hydrogen atom or methyl,
A is $CH_2$, O or NH, preferably O,
m is zero or 1, and
$R^\delta$ is a heterocyclic radical such as a pyrimidinyl radical or a triazinyl radical.

Preference is given to phenylsulfonylureas of the formula (III) and/or their salts

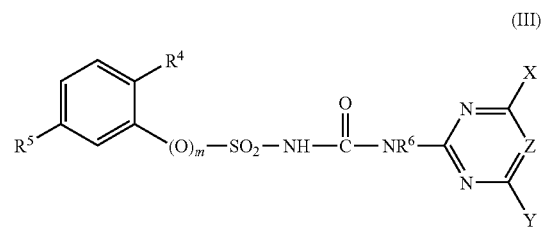  (III)

in which
$R^4$ is $C_1$-$C_4$-alkoxy, preferably $C_2$-$C_4$-alkoxy, or CO—$R^a$ in which $R^a$ is OH, $C_1$-$C_4$-alkoxy or $NR^bR^c$ in which $R^b$ and $R^c$ independently of one another are identical or different and are H or $C_1$-$C_4$-alkyl,
$R^5$ is halogen, preferably iodine, or $(A)_n$-$NR^dR^e$ where n is zero or 1, A is a group CR'R" in which R' and R" independently of one another are identical or different radicals from the group consisting of H and $C_1$-$C_4$-alkyl, $R^d$ is H or $C_1$-$C_4$-alkyl and $R^e$ is an acyl radical, such as formyl, or $C_1$-$C_4$-alkylsulfonyl, and in the case that $R^4$ is $C_1$-$C_4$-alkoxy, preferably $C_2$-$C_4$-alkoxy, $R^5$ may also be H, $R^6$ is H or $C_1$-$C_4$-alkyl, m is zero or 1, X and Y are identical or different and independently of one another are halogen or NR'R", where R' and R" are identical or different and are H or $C_1$-$C_4$-alkyl, or $C_1$-$C_6$-alkyl, $C_1$-$C_6$-alkoxy, $C_1$-$C_6$-alkylthio, $C_3$-$C_6$-cycloalkyl, $C_2$-$C_6$-alkenyl, $C_2$-$C_6$-alkynyl, $C_3$-$C_6$-alkenyloxy or $C_3$-$C_6$-alkynyloxy, where each of the eight last mentioned radicals is unsubstituted or substituted by one or more radicals from the group consisting of halogen, $C_1$-$C_4$-alkoxy and $C_1$-$C_4$-alkylthio, preferably $C_1$-$C_4$-alkyl or $C_1$-$C_4$-alkoxy, and Z is CH or N.

Particular preference is given to phenylsulfonylureas of the formula (III) and/or their salts in which a) $R^4$ is CO—($C_1$-$C_4$-alkoxy), $R^5$ is halogen, preferably iodine, or $R^5$ is $CH_2NHR^e$, where $R^e$ is an acyl radical, preferably $C_1$-$C_4$-alkylsulfonyl, and m is zero, b) $R^4$ is CO—N($C_1$-$C_4$-alkyl)$_2$, $R^5$ is NHR$^e$, where R$^e$ is an acyl radical, preferably formyl, and m is zero, or c) $R^4$ is $C_2$-$C_4$-alkoxy, $R^5$ is H and m is 1.

Typical phenylsulfonylureas are, inter alia, the compounds listed below and their salts, such as the sodium salts: bensulfuron-methyl, chlorimuron-ethyl, chlorsulfuron, cinosulfuron, cyclosulfamuron, ethametsulfuron-methyl, ethoxysulfuron and its sodium salt, metsulfuron-methyl, oxasulfuron, primisulfuron-methyl, prosulfuron, sulfometuron-methyl, triasulfuron, tribenuron-methyl, triflusulfuron-methyl, tritosulfuron, iodosulfuron-methyl and its sodium salt, mesosulfuron-methyl and its sodium salt and foramsulfuron and its sodium salt.

Particularly preferred phenylsulfonamides are: iodosulfuron-methyl (A1.1) and its salts, such as the sodium salt (A1.2), mesosulfuron-methyl (A2.1) and its salts, such as the sodium salt (A2.2), foramsulfuron (A3.1) and its salts, such as the sodium salt (A3.2), flucarbazone (A4.1) and its salts, such as the sodium salt (A4.2), propoxycarbazone (A5.1) and its salts, such as the sodium salt (A5.2) and ethoxysulfuron (A6.1) and its salts, such as the sodium salt (A6.2), metsulfuron-methyl (A7.1) and its salts, such as the sodium salt (A7.2), tribenuron-methyl (A8.1) and its salts, such as the sodium salt (A8.2), chlorsulfuron (A9.1) and its salts, such as the sodium salt (A9.2).

Suitable heteroarylsulfonamides A) are, for example, compounds from the group of the heteroarylsulfonylaminocarbonyltriazolinones or the heteroarylsulfonylureas, preferably from the group of the heteroarylsulfonylureas. The term heteroarylsulfonylyreas is to be understood as including those sulfonylureas in which the heteroaryl group is attached to the sulfone group (SO$_2$) via a spacer such as CH$_2$, O or NH.

Suitable heteroarylsulfonamides are, for example, sulfonamides of the formula (IV) and/or their salts

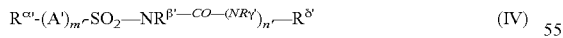   (IV)

in which $R^{\alpha'}$ is an unsubstituted or substituted heteroaryl radical, where the heteroaryl radical including substituents has 1-30 carbon atoms, preferably 1-20 carbon atoms, $R^{\beta'}$ is a hydrogen atom or an unsubstituted or substituted hydrocarbon radical which, including substituents, has 1-10 carbon atoms, for example unsubstituted or substituted $C_1$-$C_6$ alkyl, preferably a hydrogen atom or methyl, $R^{\gamma'}$ is a hydrogen atom or an unsubstituted or substituted hydrocarbon radical which, including substituents, has 1-10 carbon atoms, for example unsubstituted or substituted $C_1$-$C_6$ alkyl, preferably a hydrogen atom or methyl, A' is CH$_2$, O or NH, preferably O, m' is zero or 1, n' is zero or 1, preferably 1, and $R^{\delta'}$ is a heterocyclic radical such as a pyrimidinyl radical, a triazinyl radical or a triazolinone radical.

Preferred heteroarylsulfonamides are heteroarylsulfonylureas, for example sulfonylureas of the formula (V) and/or their salts

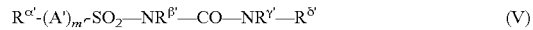   (V)

in which $R^{\alpha'}$ is an unsubstituted or substituted heteroaryl radical, where the heteroaryl radical including substituents has 1-30 carbon atoms, preferably 1-20 carbon atoms, $R^{\beta'}$ is a hydrogen atom or an unsubstituted or substituted hydrocarbon radical which, including substituents, has 1-10 carbon atoms, for example unsubstituted or substituted $C_1$-$C_6$ alkyl, preferably a hydrogen atom or methyl, $R^{\gamma'}$ is a hydrogen atom or an unsubstituted or substituted hydrocarbon radical which, including substituents, has 1-10 carbon atoms, for example unsubstituted or substituted $C_1$-$C_6$ alkyl, preferably a hydrogen atom or methyl, A' is CH$_2$, O or NH, preferably O, m' is zero or 1, and $R^{\delta'}$ is a heterocyclic radical such as a pyrimidinyl radical or a triazinyl radical.

Particular preference is given to heteroarylsulfonamides of the formula (VI) mentioned below

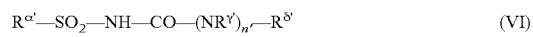   (VI)

in which $R^{\alpha'}$ is a substituted heteroaryl radical, such as substituted pyridyl, thienyl, pyrazolyl or imidazolyl, $R^{\gamma'}$ is H, ($C_1$-$C_3$)-alkyl, optionally substituted by halogen (F, Cl, Br, I) or halo-($C_1$-$C_3$) alkoxy, preferably H or methyl, when n' is 1, $R^{\delta'}$ is a pyrimidinyl radical or a triazinyl radical, preferably

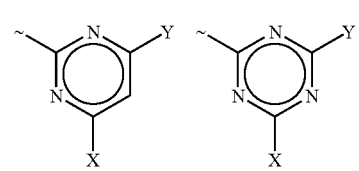

and when n' is zero, $R^{\delta'}$ is a triazolinone radical, preferably

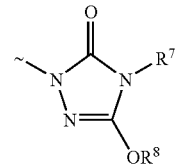

$R^7$ is ($C_1$-$C_{10}$)-alkyl which is optionally substituted by halogen (F, Cl, Br, I) or ($C_1$-$C_3$)-haloalkyl, $R^8$ is ($C_1$-$C_{10}$)-alkyl which is optionally substituted by halogen (F, Cl, Br, I) or ($C_1$-$C_3$)-haloalkyl, X and Y are identical or different and independently of one another are halogen or NR'R", where R' and R" are identical or different and are H or $C_1$-$C_4$-alkyl, or $C_1$-$C_6$ alkyl, $C_1$-$C_6$alkoxy, $C_1$-$C_6$alkylthio, $C_3$-$C_6$-cycloalkyl, $C_2$-$C_6$alkenyl, $C_2$-$C_6$ alkynyl, $C_3$-$C_6$-alkenyloxy or $C_3$-$C_6$-alkynyloxy, where each of the eight lastmentioned radicals is unsubstituted or substituted by one or more radicals from the group consisting of halogen, $C_1$-$C_4$-alkoxy and $C_1$-$C_4$-alkylthio, preferably $C_1$-$C_4$-alkyl or $C_1$-$C_4$-alkoxy.

Particularly preferably. $R^\alpha$ is

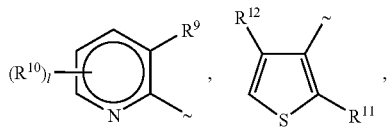

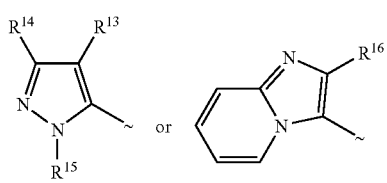

in which $R^9$ is $(C_1$-$C_6)$-alkyl, $(C_1$-$C_6)$-alkoxy, $(C_2$-$C_6)$-alkenyloxy, $(C_2$-$C_6)$-alkynyloxy, $(C_1$-$C_6)$-alkylsulfonyl, $(C_1$-$C_6)$-alkylcarbonyl, $(C_1$-$C_6)$-alkoxycarbonyl, $(C_2$-$C_6)$-alkenyloxycarbonyl, $(C_2$-$C_6)$-alkynyloxycarbonyl, CONR'R", halo-$(C_1$-$C_6)$-alkyl, halo-$(C_1$-$C_6)$-alkoxy, halo-$(C_2$-$C_6)$-alkenyloxy, halo-$(C_2$-$C_6)$-alkynyloxy, halo-$(C_1$-$C_6)$-alkylsulfonyl, halo-$(C_1$-$C_6)$-alkylcarbonyl, halo-$(C_1$-$C_6)$-alkoxycarbonyl, halo-$(C_2$-$C_6)$-alkenyloxycarbonyl, halo-$(C_2$-$C_6)$-alkynyloxycarbonyl, $R^{10}$ is H, $(C_1$-$C_3)$-alkyl, $(C_1$-$C_3)$-alkoxy, halo-$(C_1$-$C_3)$-alkyl, halo-$(C_1$-$C_3)$-alkoxy or halogen (F, Cl, Br, I), l is zero or 1, $R^{11}$ is $(C_1$-$C_6)$-alkyl, $(C_1$-$C_6)$-alkoxy, $(C_2$-$C_6)$-alkenyloxy, $(C_2$-$C_6)$-alkynyloxy, $(C_1$-$C_6)$-alkylsulfonyl, $(C_1$-$C_6)$-alkylcarbonyl, $(C_1$-$C_6)$-alkoxycarbonyl, $(C_2$-$C_6)$-alkenyloxycarbonyl, $(C_2$-$C_6)$-alkynyloxycarbonyl, halo-$(C_1$-$C_6)$-alkyl, halo-$(C_1$-$C_6)$-alkoxy, halo-$(C_2$-$C_6)$-alkenyloxy, halo-$(C_2$-$C_6)$-alkynyloxy, halo-$(C_1$-$C_6)$-alkylsulfonyl, halo-$(C_1$-$C_6)$-alkylcarbonyl, halo-$(C_1$-$C_6)$-alkoxycarbonyl, halo-$(C_2$-$C_6)$-alkenyloxycarbonyl, halo-$(C_2$-$C_6)$-alkynyloxycarbonyl, CONR'R", $R^{12}$ is halogen (F, Cl, Br, I), $(C_1$-$C_6)$-alkyl, $(C_1$-$C_6)$-alkoxy, $(C_1$-$C_6)$-alkylsulfonyl, $(C_1$-$C_6)$-alkoxycarbonyl, $(C_2$-$C_6)$-alkenyloxycarbonyl, $(C_2$-$C_6)$-alkynyloxycarbonyl, halo-$(C_1$-$C_6)$-alkyl, halo-$(C_1$-$C_6)$-alkoxy, halo-$(C_1$-$C_6)$-alkylsulfonyl, halo-$(C_1$-$C_6)$-alkoxycarbonyl, halo-$(C_2$-$C_6)$-alkenyloxycarbonyl, halo-$(C_2$-$C_6)$-alkynyloxycarbonyl, $R^{13}$ is $(C_1$-$C_6)$-alkoxycarbonyl, $(C_2$-$C_6)$-alkenyloxycarbonyl, $(C_2$-$C_6)$-alkynyl-oxycarbonyl, $(C_1$-$C_6)$-alkyl, $(C_1$-$C_6)$-alkoxy, $(C_1$-$C_6)$-alkylsulfonyl, halo-$(C_1$-$C_6)$-alkoxycarbonyl, halo-$(C_2$-$C_6)$-alkenyloxycarbonyl, halo-$(C_2$-$C_6)$-alkynyloxycarbonyl, halo-$(C_1$-$C_6)$-alkyl, halo-$(C_1$-$C_6)$-alkoxy, halo-$(C_1$-$C_6)$-alkylsulfonyl, halogen (F, Cl, Br, I), CONR'R", or $R^{13}$ is a heterocyclic ring, which may be saturated, unsaturated or aromatic and which preferably contains 4-6 ring atoms and one or more heteroatoms from the group consisting of N, O and S and which may be unsubstituted or substituted by one or more substituents, preferably from the group consisting of ($C_1$-$C_3$)-alkyl, ($C_1$-$C_3$)-alkoxy, halo-($C_1$-$C_3$)-alkyl, halo-($C_1$-$C_3$)-alkoxy and halogen, particularly preferably

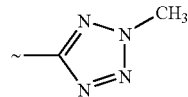

$R^{14}$ is H, halogen (F, C, Br, I), $(C_1$-$C_6)$-alkyl, halo-$(C_1$-$C_6)$-alkyl, $R^{15}$ is H, $(C_1$-$C_6)$-alkyl, halo-$(C_1$-$C_6)$-alkyl, $R^{16}$ is $(C_1$-$C_6)$-alkyl, $(C_1$-$C_6)$-alkoxy, $(C_2$-$C_6)$-alkenyloxy, $(C_2$-$C_6)$-alkynyloxy, $(C_1$-$C_6)$-alkylsulfonyl, $(C_1$-$C_6)$-alkylcarbonyl, $(C_1$-$C_6)$-alkoxycarbonyl, $(C_2$-$C_6)$-alkenyloxycarbonyl, $(C_2$-$C_6)$-alkynyloxycarbonyl, halo-$(C_1$-$C_6)$-alkyl, halo-$(C_1$-$C_6)$-alkoxy, halo-$(C_2$-$C_6)$-alkenyloxy, halo-$(C_2$-$C_6)$-alkynyloxy, halo-$(C_1$-$C_6)$-alkylsulfonyl, halo-$(C_1$-$C_6)$-alkylcarbonyl, halo-$(C_1$-$C_6)$-alkoxycarbonyl, halo-$(C_2$-$C_6)$-alkenyloxycarbonyl, halo-$(C_2$-$C_6)$-alkynyloxycarbonyl, CONR'R", in particular $SO_2$-ethyl, and R' and R" independently of one another are H, $(C_1$-$C_6)$-alkyl, halo-$(C_1$-$C_6)$-alkyl, $(C_2$-$C_6)$-alkenyl, $(C_2$-$C_6)$-haloalkenyl, $(C_2$-$C_6)$-alkynyl, $(C_2$-$C_6)$-haloalkynyl, or NR'R" forms a heterocyclic ring which may be saturated, unsaturated or aromatic and which preferably contains 4-6 ring atoms and one or more heteroatoms from the group consisting of N, O and S and which may be unsubstituted or substituted by one or more substituents, preferably from the group consisting of ($C_1$-$C_3$)-alkyl, ($C_1$-$C_3$)-alkoxy, halo-($C_1$-$C_3$)-alkyl, halo-($C_1$-$C_3$)-alkoxy and halogen.

Particularly preferred heteroarylsulfonylureas are, for example, nicosulfuron (A10.1) and its salts, such as the sodium salt (A10.2), rimsulfuron (A11.1) and its salts, such as the sodium salt (A11.2), thifensulfuron-methyl (A12.1) and its salts, such as the sodium salt (A12.2), pyrazosulfuron-ethyl (A13.1) and its salts, such as the sodium salt (A13.2), flupyrsulfuron-methyl (A14.1) and its salts, such as the sodium salt (A14.2), sulfosulfuron (A15.1) and its salts, such as the sodium salt (A15.2), trifloxysulfuron (A16.1) and its salts, such as the sodium salt (A16.2), azimsulfuron (A17.1) and its salts, such as the sodium salt (A17.2), flazasulfuron (A18.1) and its salts, such as the sodium salt (A18.2) and flucetosulfuron (1-[3-[[[[(4,6-dimethoxy-2-pyrimidinyl)amino]carbonyl]amino]sulfonyl]-2-pyridinyl]-2-fluoropropyl methoxyacetate (A19.1)) and its salts, such as the sodium salt (A 19.2).

Particularly preferred heteroarylsulfonylaminocarbonyltriazolinones are thiencarbazone-methyl (A20.1) and its salts, such as the sodium salt (A20.2).

Other suitable ALS inhibitors are, for example, imidazolinones, for example methyl 2-(4-isopropyl-4-methyl-5-oxo-2-imidazolin-2-yl)-5-methylbenzoate and 2-(4-isopropyl-4-methyl-5-oxo-2-imidazolin-2-yl)-4-methylbenzoic acid (imazamethabenz), 5-ethyl-2-(4-isopropyl-4-methyl-5-oxo-2-imidazolin-2-yl)-pyridine-3-carboxylic acid (imazethapyr), 2-(4-isopropyl-4-methyl-5-oxo-2-imidazolin-2-yl)quinoline-3-carboxylic acid (imazaquin), 2-(4-isopropyl-4-methyl-5-oxo-2-imidazolin-2-yl)pyridine-3-carboxylic acid (imazapyr), 5-methyl-2-(4-isopropyl-4-methyl-5-oxo-2-imidazolin-2-yl)pyridine-3-carboxylic acid (imazethamethapyr);

triazolopyrimidinesulfonamides, for example

N-(2,6-dichloro-3-methylphenyl)-5,7-dimethoxy-1,2,4-triazolo[1,5-c]pyrimidine-2-sulfonamide,
N-(2,6-difluorophenyl)-7-fluoro-5-methoxy-1,2,4-triazolo [1,5-c]pyrimidine-2-sulfonamide,
N-(2,6-dichloro-3-methylphenyl)-7-chloro-5-methoxy-1,2, 4-triazolo[1,5-c]pyrimidine-2-sulfonamide,
N-(2-chloro-6-methoxycarbonyl)-5,7-dimethyl-1,2,4-triazolo[1,5-c]pyrimidine-2-sulfonamide (EP-A 0 343 752, U.S. Pat. No. 4,988,812),
N-(2,6-difluorophenyl)-7-methyl-1,2,4-triazolo[1,5-c]pyrimidine-2-sulfonamide,
2',6'-difluoro-5-methyl[1,2,4]triazolo[1,5-a]pyrimidine-2-sulfonanilide (flumetsulam, CAS number 98967-40-9) (A21),
N-(5,7-dimethoxy[1,2,4]triazolo[1,5-a]pyrimidin-2-yl)-2-methoxy-4-(trifluoromethyl)-3-pyridinesulfonamide (pyroxulam, CAS number 422556-08-9) (A22),
2-(2,2-difluoroethoxy)-N-(5,8-dimethoxy[1,2,4]triazolo-[1, 5-c]pyrimidin-2-yl)-6-(trifluoromethyl)benzenesulfonamide (penoxsulam, CAS number 219714-96-2) (A23),
2',6',8-trifluoro-5-methoxy[1,2,4]triazolo[1,5-c]pyrimidine-2-sulfonanilide (florasulam, CAS number 145701-23-1) (A24),
2',6'-dichloro-5,7-dimethoxy-3'-methyl[1,2,4]triazolo[1,5-a] pyrimidine-2-sulfonanilide (metosulam, CAS number 139528-85-1) (A25),
N-(2,6-dichlorophenyl)-5-ethoxy-7-fluoro[1,2,4]triazolo[1, 5-c]pyrimidine-2-sulfonamide (diclosulam, CAS number 145701-21-9) (A26),
methyl 3-chloro-2-(5-ethoxy-7-fluoro[1,2,4]triazolo[1,5-c] pyrimidin-2-ylsulfonamido)benzoate, (cloransulam-methyl, CAS number 147150-35-4) (A27);
pyrimidinyloxypyridinecarboxylic acid or pyrimidinyloxybenzoic acid derivatives, for example
benzyl 3-(4,6-dimethoxypyrimidin-2-yl)oxypyridine-2-carboxylate (EP-A-0 249 707),
methyl 3-(4,6-dimethoxypyrimidin-2-yl)oxypyridine-2-carboxylate (EP-A-0 249 707),
2,6-bis[(4,6-dimethoxypyrimidin-2-yl)oxy]benzoic acid (EP-A 0 321 846),
1-(ethoxycarbonyloxyethyl) 2,6-bis[(4,6-dimethoxypyrimidin-2-yl)oxy]benzoate (EP-A 0 472 113).

Very particularly preferred ALS inhibitors A) are sulfonamides, for example iodosulfuron-methyl (A1.1), iodosulfuron-methyl-sodium (A1.2), mesosulfuron-methyl (A2.1), mesosulfuron-methyl-sodium (A2.2), flucarbazone (A4.1), flucarbazone-sodium (A4.2), propoxycarbazone (A5.1) and propoxycarbazone-sodium (A5.2).

The active compounds listed above are known, for example, from "The Pesticide Manual", 14th edition (2006), The British Crop Protection Council or the literature references listed after the individual active compounds.

For the purpose of the present invention, the ALS inhibitors A) present in the combinations according to the invention are in each case to be understood as meaning all use forms, such as acids, esters, salts and isomers, such as stereoisomers and optical isomers. Thus, in addition to the neutral compounds, their salts with inorganic and/or organic counterions are in each case meant to be included. Thus, sulfonamides are capable of forming salts, for example, in which the hydrogen of the —$SO_2$—NH group is replaced by an agriculturally suitable cation. These salts are, for example, metal salts, in particular alkali metal salts or alkaline earth metal salts, in particular sodium and potassium salts, or else ammonium salts or salts with organic amines. Salt formation may also take place by addition of an acid to basic groups, such as, for example, amino and alkylamino. Acids suitable for this purpose are strong inorganic and organic acids, for example HCl, HBr, $H_2SO_4$ or $HNO_3$. Preferred esters are the alkyl esters, in particular the $C_1$-$C_{10}$-alkyl esters, such as methyl esters.

Whenever the term "acyl radical" is used in this description, this means the radical of an organic acid which is formally formed by removing an OH group from the organic acid, for example the radical of a carboxylic acid and radicals of acids derived therefrom, such as thiocarboxylic acid, unsubstituted or N-substituted iminocarboxylic acids or the radicals of carbonic monoesters, unsubstituted or N-substituted carbamic acids, sulfonic acids, sulfinic acids, phosphonic acids, phosphinic acids.

An acyl radical is preferably formyl or acyl from the group consisting of CO—$R^z$, CS—$R^z$, CO—$OR^z$, CS—$OR^z$, CS—$SR^z$, $SOR^z$ and $SO_2R^z$, where $R^z$ is in each case a $C_1$-$C_{10}$-hydrocarbon radical, such as $C_1$-$C_{10}$-alkyl or $C_6$-$C_{10}$-aryl, which is unsubstituted or substituted, for example by one or more substituents from the group consisting of halogen, such as F, Cl, Br, I, alkoxy, haloalkoxy, hydroxyl, amino, nitro, cyano and alkylthio, or $R^z$ is aminocarbonyl or aminosulfonyl, where the two lastmentioned radicals are unsubstituted, N-monosubstituted or N,N-disubstituted, for example by substituents from the group consisting of alkyl and aryl. Acyl is, for example, formyl, haloalkylcarbonyl, alkylcarbonyl, such as ($C_1$-$C_4$)-alkyl-carbonyl, phenylcarbonyl, where the phenyl ring may be substituted, or alkyloxy-carbonyl, such as ($C_1$-$C_4$)-alkyloxycarbonyl, phenyloxycarbonyl, benzyloxycarbonyl, alkylsulfonyl, such as ($C_1$-$C_4$)-alkylsulfonyl, alkylsulfinyl, such as $C_1$-$C_4$-(alkylsulfinyl), N-alkyl-1-iminoalkyl, such as N—($C_1$-$C_4$)-1-imino-($C_1$-$C_4$)-alkyl, and other radicals of organic acids.

A hydrocarbon radical is a straight-chain, branched or cyclic and saturated or unsaturated aliphatic or aromatic hydrocarbon radical, for example alkyl, alkenyl, alkynyl, cycloalkyl, cycloalkenyl or aryl.

A hydrocarbon radical has preferably 1 to 40 carbon atoms, with preference 1 to 30 carbon atoms; with particular preference, a hydrocarbon radical is alkyl, alkenyl or alkynyl having up to 12 carbon atoms or cycloalkyl having 3, 4, 5, 6 or 7 ring atoms or phenyl.

Aryl is a mono-, bi- or polycyclic aromatic system, for example phenyl, naphthyl, tetrahydronaphthyl, indenyl, indanyl, pentalenyl, fluorenyl and the like, preferably phenyl.

A heterocyclic radical or ring (heterocyclyl) can be saturated, unsaturated or heteroaromatic and unsubstituted or substituted; it preferably contains one or more heteroatoms in the ring, preferably from the group consisting of N, O and S; it is preferably an aliphatic heterocyclyl radical having 3 to 7 ring atoms or a heteroaromatic radical having 5 or 6 ring atoms and contains 1, 2 or 3 heteroatoms. The heterocyclic radical can, for example, be a heteroaromatic radical or ring (heteroaryl), such as, for example, a mono-, bi- or polycyclic aromatic system in which at least one ring contains one or more heteroatoms, for example pyridyl, pyrimidinyl, pyridazinyl, pyrazinyl, triazinyl, thienyl, thiazolyl, oxazolyl, furyl, pyrrolyl, pyrazolyl and imidazolyl, or it is a partially or fully hydrogenated radical, such as oxiranyl, oxetanyl, pyrrolidyl, piperidyl, piperazinyl, triazolyl, dioxolanyl, morpholinyl, tetrahydrofuryl. Preference is given to pyrimidinyl and triazinyl. Suitable substituents for a substituted heterocyclic radical are the substituents specified later on below, and additionally also oxo. The oxo group may also occur on the hetero-ring atoms which are able to exist in different oxidation states, as in the case of N and S, for example.

Substituted radicals, such as substituted hydrocarbon radicals, for example substituted alkyl, alkenyl, alkynyl, aryl, phenyl and benzyl, or substituted heterocyclyl or heteroaryl, are, for example, a substituted radical which is derived from the unsubstituted parent compound, where the substituents are, for example, one or more, preferably 1, 2 or 3, radicals from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, haloalkylsulfinyl, alkylsulfonyl, haloalkylsulfonyl and, in the case of cyclic radicals, also alkyl and haloalkyl, and unsaturated aliphatic radicals which correspond to the saturated hydrocarbon-containing radicals mentioned, such as alkenyl, alkynyl, alkenyloxy, alkynyloxy, etc. Among the radicals with carbon atoms, preference is given to those having 1 to 4 carbon atoms, in particular 1 or 2 carbon atoms. Preference is generally given to substituents from the group consisting of halogen, for example fluorine and chlorine, $(C_1-C_4)$-alkyl, preferably methyl or ethyl, $(C_1-C_4)$-haloalkyl, preferably trifluoromethyl, $(C_1-C_4)$-alkoxy, preferably methoxy or ethoxy, $(C_1-C_4)$-haloalkoxy, nitro and cyano. Particular preference is given here to the substituents methyl, methoxy and chlorine.

Unsubstituted or substituted phenyl is preferably phenyl which is unsubstituted or mono- or polysubstituted, preferably substituted up to three times, by identical or different radicals, preferably from the group consisting of halogen, $(C_1-C_4)$-alkyl, $(C_1-C_4)$-alkoxy, $(C_1-C_4)$-haloalkyl, $(C_1-C_4)$-haloalkoxy and nitro, for example o-, m- and p-tolyl, dimethylphenyl, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

Cycloalkyl is a carbocyclic saturated ring system having preferably 3-6 carbon atoms, for example cyclopropyl, cyclobutyl, cyclopentyl or cyclohexyl.

The carbon skeleton of the carbon-containing radicals, such as alkyl, alkoxy, haloalkyl, haloalkoxy, alkylamino and alkylthio and the corresponding unsaturated and/or substituted radicals can in each case be straight-chain or branched. In these radicals, preference is given to the lower carbon skeletons having, for example, 1 to 6 carbon atoms and, in the case of unsaturated groups, 2 to 6 carbon atoms, unless specified otherwise. Alkyl radicals, also in the composite meanings such as alkoxy, haloalkyl, etc., are, for example, methyl, ethyl, n- or isopropyl, n-, iso-, t- or 2-butyl, pentyls, hexyls, such as n-hexyl, isohexyl and 1,3-dimethylbutyl, heptyls, such as n-heptyl, 1-methylhexyl and 1,4-dimethylpentyl; alkenyl and alkynyl radicals have the meaning of the possible unsaturated radicals which correspond to the alkyl radicals; alkenyl is, for example, allyl, 1-methylprop-2-en-1-yl, 2-methyl-prop-2-en-1-yl, but-2-en-1-yl, but-3-en-1-yl, 1-methyl-but-3-en-1-yl and 1-methyl-but-2-en-1-yl; alkynyl is, for example, propargyl, but-2-yn-1-yl, but-3-yn-1-yl, 1-methyl-but-3-yn-1-yl.

Halogen is, for example, fluorine, chlorine, bromine or iodine. Haloalkyl, -alkenyl and -alkynyl are alkyl, alkenyl and alkynyl, respectively, which are partially or fully substituted by halogen, preferably by fluorine, chlorine and/or bromine, in particular by fluorine or chlorine, for example $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and other halogen-substituted radicals.

Suitable components B) are agrochemically active compounds, preferably fungicidally active compounds, from the group of the triazoles, pyrazoles or triazolinethiones, preferably from the group of the triazoles, for example the active compounds mentioned below (the CAS number of at least one preferred form, in particular a commercial form, is stated after each of the compound names):

B1: azaconazole (60207-31-0), B2: bromuconazole (116255-48-2),
B3: cyproconazole (113096-99-4), B4: diclobutrazole (75736-33-3),
B5: difenoconazole (119446-68-3), B6: diniconazole (83657-24-3),
B7: diniconazole-M (83657-18-5), B8: epoxiconazole (106325-08-0),
B9: etaconazole (60207-93-4), B10: fenbuconazole (114369-43-6),
B11: fluquinconazole (136426-54-5), B12: flusilazole (85509-19-9),
B13: furconazole (112839-33-5), B14: hexaconazole (79983-71-4),
B15: imibenconazole (86598-92-7), B16: ipconazole (125225-28-7),
B17: metconazole (125116-23-6), B18: paclobutrazol (76738-62-0),
B19: penconazole (66246-88-6), B20: propiconazole (60207-90-1),
B21: prothioconazole (178928-70-6), B22: quinconazole (13970-75-8),
B23: simeconazole (149508-90-7), B24: tebuconazole (107534-96-3),
B25: tetraconazole (112281-77-3), B26: triticonazole (131983-72-7),
B27: uniconazole (83657-22-1), B28: viniconazole (77174-66-4),
B29: voriconazole (137234-62-9), B30: (1-(4-chlorophenyl)-2-(1H-1,2,4-triazol-1-yl)cycloheptanol (129586-32-9),
B31: triadimenol (55219-65-3; 89482-17-7; 82200-72-4),
B32: triadimefon (43121-43-3), B33: bitertanol (70585-36-3; 70585-38-5; 55179-31-2), B34: flutriafol (76674-21-0), B35: myclobutanil (88671-89-0).

Particularly preferred azoles B) are cyproconazole (B3), epoxiconazole (B8), fluquinconazole (B11), propiconazole (B20), prothioconazole (B21), tebuconazole (B24) and myclobutanil (B35).

In general, the herbicide/azole combinations according to the invention comprise an effective amount of components A) and B) and may additionally comprise further components, for example agrochemically active compounds of a different type and/or additives and/or formulation auxiliaries customary in crop protection, or may be used together with these.

In a preferred embodiment, the herbicide/azole combinations according to the invention comprise a synergistically effective amount of components A) and B). The synergistic effects, in particular synergistic herbicidal effects, can be observed, for example, when applying the active compounds A) and B) together; however, they can frequently also be observed when the active compounds are applied at different times (splitting). It is also possible to apply the individual active compounds or the herbicide/azole combinations in a plurality of portions (sequential application), for example pre-emergence applications followed by post-emergence applications or early post-emergence applications followed by medium or late post-emergence applications. Preference is given here to the joint or almost simultaneous application of the active compounds of the herbicide/azole combination according to the invention.

The synergistic effects permit a reduction of the application rates of the individual active compounds, a higher efficacy at the same application rate, the control of species which were as yet uncontrolled (gaps), an extension of the period of application and/or a reduction in the number of individual applications required and—as a result for the user—weed control systems which are more advantageous economically and ecologically.

The formulae (I)-(VI) mentioned embrace all stereoisomers and their mixtures, in particular also racemic mixtures, and—if enantiomers are possible—the respective enantiomer which is biologically active. The compounds of the formulae (I)-(VI) are capable of forming salts, for example those in which the hydrogen of the —$SO_2$—NH group is replaced by an agriculturally suitable cation. These salts are, for example, metal salts, in particular alkali metal salts or alkaline earth metal salts, in particular sodium and potassium salts, or else ammonium salts or salts with organic amines. Salt formation may also take place by addition of an acid to basic groups, such as, for example, amino and alkylamino. Acids suitable for this purpose are strong inorganic and organic acids, for example HCl, HBr, $H_2SO_4$ or $HNO_3$.

The herbicidally active compounds A) are able to inhibit the enzyme acetolactate synthase (ALS) and thus the protein synthesis in plants. The application rate of the active compounds A) can vary within a wide range, for example between 0.001 and 0.5 kg of AS/ha (hereinbelow, AS/ha means "active substance per hectare"=based on 100% pure active compound). Applied at application rates of from 0.01 to 0.2 kg of AS/ha of the active compounds A), preferably the active compounds A1.1, A1.2, A2.1, A2.2, A4.1, A4.2, A5.1 and A5.2, a relatively broad spectrum of annual and perennial broad-leaved weeds, weed grasses and Cyperaceae is controlled by the pre- and post-emergence methods. In the combinations according to the invention, the application rates are generally lower, for example in the range of from 0.5 to 120 g of AS/ha, preferably from 1 to 50 g of AS/ha.

The application rate of the agrochemically active compounds B) can vary within wide limits, for example from 0.001 to 0.5 kg of AS/ha. The application rate of the active compounds B), preferably the active compounds B3, B8, B11, B20, B21, B24 and B35, is preferably in the range from 0.01 to 0.25 kg of AS/ha.

In the herbicide/azole combinations according to the invention, the components A) and B) are preferably present in a synergistically effective amount. The application rate ratio of the components A):B) can vary within wide limits, for example from 1:50 to 5:1, preferably from 1:25 to 2.5:1, particularly preferably from 1:15 to 2:1. The active compounds can generally be formulated as a wettable powder (WP), as water-dispersible granules (WDG), as water-emulsifiable granules (WEG), as a suspoemulsion (SE), as an oil dispersion (OD), as a suspension concentrate (SC or FS), as an emulsifiable concentrate (EC), as aqueous solutions (SL), as emulsions (EW).

The application rate ratios A): B) which are generally used are indicated above and refer to the weight ratio of the two components A) and B).

When using the active compounds A) in crop plants it may be expedient, depending on the crop plant, to apply a safener above certain application rates to reduce or avoid possible damage to the crop plant. Examples of suitable safeners are those which act as safeners in combination with ALS inhibitors, for example sulfonamide herbicides such as sulfonylureas. Suitable safeners are known, for example, from WO-A-96/14747 and the literature cited therein.

The following groups of compounds are, for example, suitable as safeners:
S1) compounds of the formula (S1)

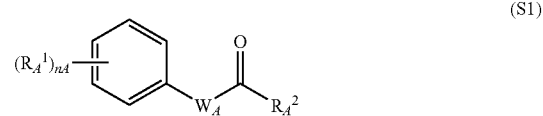

where the symbols and indices have the following meanings:
$n_A$ is a natural number from 0 to 5, preferably from 0 to 3;
$R_A^1$ is halogen, $(C_1-C_4)$-alkyl, $(C_1-C_4)$-alkoxy, nitro or $(C_1-C_4)$-haloalkyl;
$W_A$ is an unsubstituted or substituted divalent heterocyclic radical from the group consisting of partially unsaturated or aromatic five-membered heterocycles having 1 to 3 hetero ring atoms from the group consisting of N and O, where at least one nitrogen atom and at most one oxygen atom is present in the ring, preferably a radical from the group consisting of ($W_A^1$) to ($W_A^4$),

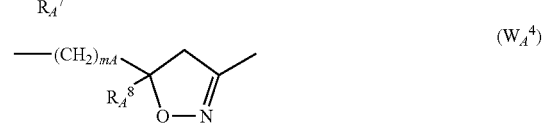

$m_A$ is 0 or 1;
$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms, preferably from the group consisting of O and S, which is attached via the nitrogen atom to the carbonyl group in (S1) and which is unsubstituted or substituted by radicals from the group consisting of $(C_1-C_4)$-alkyl, $(C_1-C_4)$-alkoxy and optionally substituted phenyl, preferably a radical of the formula $OR_A^3$, $NHR_A^4$ or $N(CH_3)_2$, in particular of the formula $OR_A^3$;
$R_A^3$ is hydrogen or an unsubstituted or substituted aliphatic hydrocarbon radical having preferably a total of 1 to 18 carbon atoms;
$R_A^4$ is hydrogen, $(C_1-C_6)$-alkyl, $(C_1-C_6)$-alkoxy or substituted or unsubstituted phenyl;
$R_A^5$ is H, $(C_1-C_8)$-alkyl, $(C_1-C_8)$-haloalkyl, $(C_1-C_4)$-alkoxy-$(C_1-C_8)$-alkyl, cyano or $COOR_A^9$ where $R_A^9$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkylsilyl;

$R_A^6$, $R_A^7$, $R_A^8$ are identical or different and are hydrogen, $(C_1-C_8)$-alkyl, $(C_1-C_8)$-haloalkyl, $(C_3-C_{12})$-cycloalkyl or substituted or unsubstituted phenyl;

preferably:

a) compounds of the type of the dichlorophenylpyrazoline-3-carboxylic acid (S1$^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds, as described in WO-A-91/07874;

b) derivatives of dichlorophenylpyrazolecarboxylic acid (S1$^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyppyrazole-3-carboxylate (S1-4) and related compounds, as described in EP-A-333 131 and EP-A-269 806;

c) derivatives of 1,5-diphenylpyrazole-3-carboxylic acid (S1$^b$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds, as described, for example, in EP-A-268554;

d) compounds of the type of the triazolecarboxylic acids (S1$^d$), preferably compounds such as fenchlorazole(-ethyl), i.e. ethyl 1-(2,4-dichlorophenyl)-5-trichloromethyl-(1H)-1,2,4-triazole-3-carboxylate (S1-7), and related compounds, as described in EP-A-174 562 and EP-A-346 620;

e) compounds of the type of the 5-benzyl- or 5-phenyl-2-isoxazoline-3-carboxylic acid or the 5,5-diphenyl-2-isoxazoline-3-carboxylic acid (S1$^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds, as described in WO-A-91/08202, or 5,5-diphenyl-2-isoxazolinecarboxylic acid (S1-10) or ethyl 5,5-diphenyl-2-isoxazolinecarboxylate (S1-11) ("isoxadifen-ethyl") or n-propyl 5,5-diphenyl-2-isoxazolinecarboxylate (S1-12) or ethyl 5-(4-fluorophenyl)-5-phenyl-2-isoxazoline-3-carboxylate (S1-13), as described in the patent application WO-A-95/07897.

S2) Quinoline derivatives of the formula (S2),

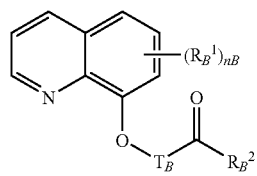

(S2)

where the symbols and indices have the following meanings:

$R_B^1$ is halogen, $(C_1-C_4)$-alkyl, $(C_1-C_4)$-alkoxy, nitro or $(C_1-C_4)$-haloalkyl;

$n_B$ is a natural number from 0 to 5, preferably from 0 to 3;

$R_B^2$ is $OR_B^3$, $SR_B^3$ or $NR_B^3R_B^4$ or a saturated
or unsaturated 3- to 7-membered heterocycle having at least one nitrogen atom and up to 3 heteroatoms, preferably from the group consisting of O and S, which is attached via the nitrogen atom to the carbonyl group in (S2) and which is unsubstituted or substituted by radicals from the group consisting of $(C_1-C_4)$-alkyl, $(C_1-C_4)$-alkoxy and optionally substituted phenyl, preferably a radical of the formula $OR_B^3$, $NHR_B^4$ or $N(CH_3)_2$, in particular of the formula $OR_B^3$;

$R_B^3$ is hydrogen or an unsubstituted or substituted aliphatic hydrocarbon radical having preferably a total of 1 to 18 carbon atoms;

$R_B^4$ is hydrogen, $(C_1-C_6)$-alkyl, $(C_1-C_6)$-alkoxy or substituted or unsubstituted phenyl;

$T_B$ is a $(C_1—$ or $C_2)$-alkanediyl chain which is unsubstituted or substituted by one or two $(C_1-C_4)$-alkyl radicals or by $[(C_1-C_3)$-alkoxy]carbonyl;

preferably:

a) compounds of the type of the 8-quinolinoxyacetic acid (S2$^a$), preferably 1-methylhexyl (5-chloro-8-quinolinoxy)acetate (common name "cloquintocet-mexyl" (S2-1), 1,3-dimethyl-but-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), alkyl (5-chloro-8-quinolinoxy)acetate (S2-7), 2-(2-propylideneiminoxy)-1-ethyl (5-chloro-8-quinolinoxy)acetate (S2-8), 2-oxo-prop-1-yl (5-chloro-8-quinolinoxy)acetate (S2-9) and related compounds, as described in EP-A-86 750, EP-A-94 349 and EP-A-191 736 or EP-A-0 492 366, and also (5-chloro-8-chinolinoxy)acetic acid (S2-10), its hydrates and salts, for example its lithium, sodium, potassium, calcium, magnesium, aluminum, iron, ammonium, quaternary ammonium, sulfonium or phosphonium salts, as described in WO-A-2002/34048;

b) compounds of the type of the (5-chloro-8-quinolinoxy) malonic acid (S2$^b$), preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

S3) Compounds of the formula (S3)

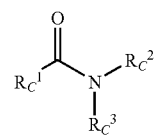

(S3)

where the symbols and indices have the following meanings:

$R_C^1$ is $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl, preferably dichloromethyl;

$R_C^2$, $R_C^3$ are identical or different and are hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$-alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, substituted or unsubstituted phenyl, or $R_C^2$ and $R_C^3$ together form a substituted or unsubstituted heterocyclic ring, preferably an oxazolidine, thiazolidine, piperidine, morpholine, hexahydropyrimidine or benzoxazine ring;

preferably:

active compounds of the type of the dichloroacetamides which are frequently used as pre-emergence safeners (soil-active safeners), such as, for example, "dichlormid" (N,N-diallyl-2,2-dichloroacetamide) (S3-1), "R-29148" (3-dichloroacetyl-2,2,5-trimethyl-1,3-oxazolidine) from Stauffer (S3-2), "R-28725" (3-dichloroacetyl-2,2-dimethyl-1,3-oxazolidine) from Stauffer (S3-3),
"benoxacor" (4-dichloroacetyl-3,4-dihydro-3-methyl-2H-1,4-benzoxazine) (S3-4),
"PPG-1292" (N-allyl-N-[(1,3-dioxolan-2-yl)methyl]dichloroacetamide) from PPG Industries (S3-5),
"DKA-24" (N-allyl-N—[(allylaminocarbonyl)methyl]dichloroacetamide) from Sagro-Chem (S3-6),
"AD-67" or "MON 4660" (3-dichloroacetyl-1-oxa-3-azaspiro[4,5]decane) from Nitrokemia or Monsanto (S3-7),
"TI-35" (1-dichloroacetylazepane) from TRI-Chemical RT (S3-8),
"diclonon" (dicyclonone) or "BAS145138" or "LAB145138" (S3-9) (3-dichloroacetyl-2,5,5-trimethyl-1,3-diazabicyclo[4.3.0]nonane) from BASF,
"furilazole" or "MON 13900" ((RS)-3-dichloroacetyl-5-(2-furyl)-2,2-dimethyloxazolidine) (S3-10) and also its (R)-isomer (S3-11).

S4) N-Acylsulfonamides of the formula (S4) and their salts,

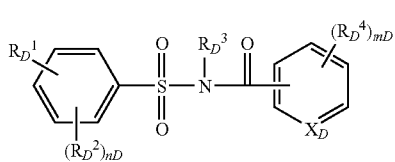

where the symbols and indices have the following meanings:
$X_D$ is CH or N;
$R_D^1$ is CO—$NR_D^5R_D^6$ or NHCO—$R_D^7$;
$R_D^2$ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulfonyl, $(C_1-C_4)$-alkoxycarbonyl or $(C_1-C_4)$-alkylcarbonyl;
$R_D^3$ is hydrogen, $(C_1-C_4)$-alkyl, $(C_2-C_4)$-alkenyl or $(C_2-C_4)$-alkynyl;
$R_D^4$ is halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkyl-sulfinyl, $(C_1-C_4)$-alkylsulfonyl, $(C_1-C_4)$-alkoxycarbonyl or $(C_1-C_4)$-alkylcarbonyl;
$R_D^5$ is hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl, phenyl or 3- to 6-membered heterocyclyl which contains $v_D$ heteroatoms from the group consisting of nitrogen, oxygen and sulfur, where the seven last-mentioned radicals are substituted by $v_D$ substituents from the group consisting of halogen, $(C_1-C_6)$-alkoxy, $(C_1-C_6)$-haloalkoxy, $(C_1-C_2)$-alkylsulfinyl, $(C_1-C_2)$-alkylsulfonyl, $(C_3-C_6)$-cycloalkyl, $(C_1-C_4)$-alkoxycarbonyl, $(C_1-C_4)$-alkylcarbonyl and phenyl and, in the case of cyclic radicals, also $(C_1-C_4)$-alkyl and $(C_1-C_4)$-haloalkyl;
$R_D^6$ is hydrogen, $(C_1-C_6)$-alkyl, $(C_2-C_6)$-alkenyl or $(C_2-C_6)$-alkynyl, where the three last-mentioned radicals are substituted by $v_D$ radicals from the group consisting of halogen, hydroxy, $(C_1-C_4)$-alkyl, $(C_1-C_4)$-alkoxy and $(C_1-C_4)$-alkylthio, or
$R_D^5$ and $R_D^6$ together with the nitrogen atom carrying them form a pyrrolidinyl or piperidinyl radical;
$R_D^7$ is hydrogen, $(C_1-C_4)$-alkylamino, di-$(C_1-C_4)$-alkylamino, $(C_1-C_6)$-alkyl, $(C_3-C_6)$-cycloalkyl, where the 2 last-mentioned radicals are substituted by $v_D$ substituents from the group consisting of halogen, $(C_1-C_4)$-alkoxy, halo-$(C_1-C_6)$-alkoxy and $(C_1-C_4)$-alkylthio and, in the case of cyclic radicals, also $(C_1-C_4)$-alkyl and $(C_1-C_4)$-haloalkyl;
$n_D$ is 0, 1 or 2;
$m_D$ is 1 or 2;
$v_D$ is 0, 1, 2 or 3;
from among these, preference is given to compounds of the type of the N-acylsulfonamides, for example of the formula (S4$^a$) below, which are known, for example, from WO-A-97/45016

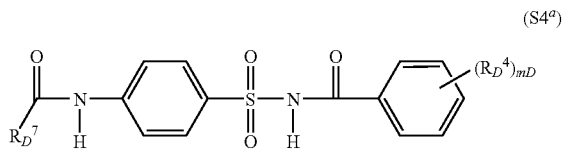

in which
$R_D^7$ is $(C_1-C_6)$-alkyl, $(C_3-C_6)$-cycloalkyl, where the 2 last-mentioned radicals are substituted by $v_D$ substituents from the group consisting of halo, $(C_1-C_4)$-alkoxy, halo-$(C_1-C_6)$-alkoxy and $(C_1-C_4)$-alkylthio and, in the case of cyclic radicals, also $(C_1-C_4)$-alkyl and $(C_1-C_4)$-haloalkyl;
$R_D^4$ is halogen, $(C_1-C_4)$-alkyl, $(C_1-C_4)$-alkoxy, $CF_3$,
$m_D$1 or 2;
$v_D$ is 0, 1, 2 or 3;
and
acylsulfamoylbenzamides, for example of the formula (S4$^b$) below, which are known, for example, from WO-A-99/16744,

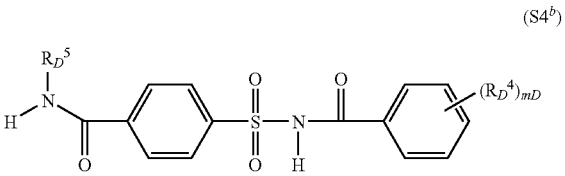

for example those in which
$R_D^5$=cyclopropyl and $(R_D^4)$=2-OMe ("cyprosulfamide", S4-1),
$R_D^5$=cyclopropyl and $(R_D^4)$=5-Cl-2-OMe (S4-2),
$R_D^5$=ethyl and $(R_D^4)$=2-OMe (S4-3),
$R_D^5$=isopropyl and $(R_D^4)$=5-Cl-2-OMe (S4-4) and
$R_D^5$=isopropyl and $(R_D^4)$=2-OMe (S4-5)
and
compounds of the type of the N-acylsulfamoylphenylureas of the formula (S4$^c$), which are known, for example, from EP-A-365484,

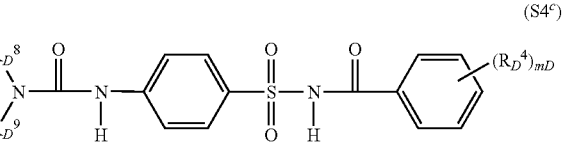

in which
$R_D^8$ and $R_D^9$ independently of one another are hydrogen, $(C_1-C_8)$-alkyl, $(C_3-C_8)$-cycloalkyl, $(C_3-C_6)$-alkenyl, $(C_3-C_6)$-alkynyl, $R_D^4$ is halogen, $(C_1-C_4)$-alkyl, $(C_1-C_4)$-alkoxy, $CF_3$,
$m_D$ is 1 or 2;
for example
1-[4-(N-2-methoxybenzoylsulfamoyl)phenyl]-3-methylurea,
1-[4-(N-2-methoxybenzoylsulfamoyl)phenyl]-3,3-dimethylurea,
1-[4-(N-4,5-dimethylbenzoylsulfamoyl)phenyl]-3-methylurea.

S5) Active compounds from the class of the hydroxyaromatics and aromatic-aliphatic carboxylic acid derivatives (S5), for example ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 2-hydroxycinnamic acid, 2,4-dichlorocinnamic acid, as described in WO-A-2004/084631, WO-A-2005/015994, WO-A-2005/016001.

S6) Active compounds from the class of the 1,2-dihydroquinoxalin-2-ones (S6), for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulfonylaminoethyl)-3-(2-thienyl)-1,2-dihydroquinoxalin-2-one, as described in WO-A-2005/112630.

S7) Compounds of the formula (S7), as described in WO-A-1998/38856,

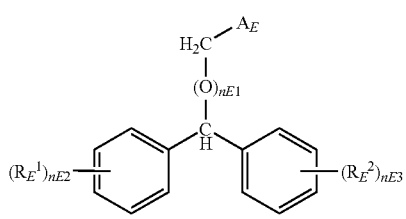
(S7)

where the symbols and indices have the following meanings:
$R_E^1$, $R_E^2$ independently of one another are halogen, $(C_1-C_4)$-alkyl, $(C_1-C_4)$-alkoxy, $(C_1-C_4)$-haloalkyl, $(C_1-C_4)$-alkylamino, di-$(C_1-C_4)$-alkylamino, nitro;
$A_E$ is $COOR_E^3$ or $COSR_E^4$
$R_E^3$, $R_E^4$ independently of one another are hydrogen, $(C_1-C_4)$-alkyl, $(C_2-C_6)$-alkenyl, $(C_2-C_4)$-alkynyl, cyanoalkyl, $(C_1-C_4)$-haloalkyl, phenyl, nitrophenyl, benzyl, halobenzyl, pyridinylalkyl or alkylammonium,
$n_E^1$ is 0 or 1;
$n_E^2$, $n_E^3$ independently of one another are 0, 1 or 2,
preferably:
  diphenylmethoxyacetic acid,
  ethyl diphenylmethoxyacetate,
  methyl diphenylmethoxyacetate (CAS Reg. No.: 41858-19-9) (S7-1).

S8) Compounds of the formula (S8), as described in WO-A-98/27049

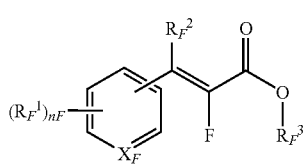
(S8)

in which
$X_F$ is CH or N,
$n_F$ is, if $X_F$=N, an integer from 0 to 4 and is, if $X_F$=CH, an integer from 0 to 5,
$R_F^1$ is halogen, $(C_1-C_4)$-alkyl, $(C_1-C_4)$-haloalkyl, $(C_1-C_4)$-alkoxy, $(C_1-C_4)$-haloalkoxy, nitro, $(C_1-C_4)$-alkylthio, $(C_1-C_4)$-alkylsulfonyl, $(C_1-C_4)$-alkoxycarbonyl, optionally substituted phenyl, optionally substituted phenoxy,
$R_F^2$ is hydrogen or $(C_1-C_4)$-alkyl,
$R_F^3$ is hydrogen, $(C_1-C_8)$-alkyl, $(C_2-C_4)$-alkenyl, $(C_2-C_4)$-alkynyl or aryl, where each of the carbon-containing radicals mentioned above is unsubstituted or substituted by one or more, preferably by up to three, identical or different radicals from the group consisting of halogen and alkoxy; or salts thereof,
preferably compounds in which
$X_F$ is CH,
$n_F$ is an integer from 0 to 2,
$R_F^1$ is halogen, $(C_1-C_4)$-alkyl, $(C_1-C_4)$-haloalkyl, $(C_1-C_4)$-alkoxy, $(C_1-C_4)$-aloalkoxy,
$R_F^2$ is hydrogen or $(C_1-C_4)$-alkyl,
$R_F^3$ is hydrogen, $(C_1-C_8)$-alkyl, $(C_2-C_4)$-alkenyl, $(C_2-C_4)$-alkynyl or aryl, where each of the carbon-containing radicals mentioned above is unsubstituted or substituted by one or more, preferably by up to three, identical or different radicals from the group consisting of halogen and alkoxy; or salts thereof, S9) Active compounds from the class of the 3-(5-tetrazolylcarbonyl)-2-quinolones (S9), for example
1,2-dihydro-4-hydroxy-1-ethyl-3-(5-tetrazolylcarbonyl)-2-quinolone (CAS Reg. No.: 219479-18-2), 1,2-dihydro-4-hydroxy-1-methyl-3-(5-tetrazolylcarbonyl)-2-quinolone (CAS Reg. No.: 95855-00-8), as described in WO-A-1999/000020.

S10) Compounds of the formula ($S10^a$) or ($S10^b$) as described in WO-A-2007/023719 and WO-A-2007/023764

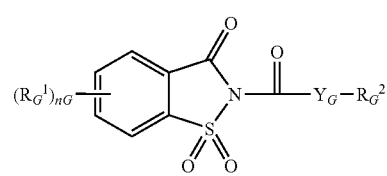
($S10^a$)

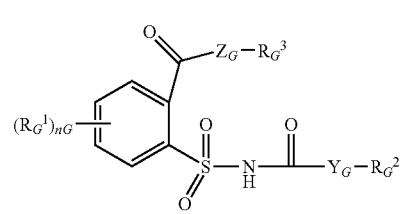
($S10^b$)

in which
$R_G^1$ is halogen, $(C_1-C_4)$-alkyl, methoxy, nitro, cyano, $CF_3$, $OCF_3$
$Y_G$, $Z_G$ independently of one another are O or S,
$n_G$ is an integer from 0 to 4,
$R_G^2$ is $(C_1-C_{16})$-alkyl, $(C_2-C_6)$-alkenyl, $(C_3-C_6)$-cycloalkyl, aryl; benzyl, halobenzyl,
$R_G^3$ is hydrogen or $(C_1-C_6)$-alkyl.

S11) Active compounds of the type of the oxyimino compounds (S11), which are known as seed dressings, such as, for example, "oxabetrinil" ((Z)-1,3-dioxolan-2-ylmethoxyimino(phenyl)acetonitrile) (S11-1), which is known as seed dressing safener for millet against metolachlor damage, "fluxofenim" (1-(4-chlorophenyl)-2,2,2-trifluoro-1-ethanone O-(1,3-dioxolan-2-ylmethyl)oxime) (S11-2), which is known as seed dressing safener for millet against metolachlor damage, and "cyometrinil" or "CGA-43089" ((Z)-cyanomethoxyimino (phenyl)acetonitrile) (S11-3), which is known as seed dressing safener for millet against metolachlor damage.

S12) Active compounds from the class of the isothiochromanones (S12), such as, for example, methyl [(3-oxo-1H-2-benzothiopyran-4(3H)-ylidene)methoxy]acetate (CAS Reg. No.: 205121-04-6) (S12-1) and related compounds from WO-A-1998/13361.

S13) One or more compounds from group (S13):
"naphthalic anhydrid" (1,8-naphthalenedicarboxylic anhydride) (S13-1), which is known as seed dressing safener for corn against thiocarbamate herbicide damage, "fenclorim" (4,6-dichloro-2-phenylpyrimidine) (S13-2), which is known as safener for retilachlor in sown rice, "flurazole" (benzyl 2-chloro-4-trifluoromethyl-1,3-thiazole-5-carboxylate) (S13-3), which is known as seed dressing safener for millet against alachlor and metolachlor damage, "CL304415" (CAS Reg. No.: 31541-57-8) (4-carboxy-3,4-dihydro-2H-1-benzopyran-4-acetic acid) (S13-4) from American Cyanamid, which is known as safener for corn against imidazolinone damage, "MG191" (CAS Reg. No.: 96420-72-3) (2-dichloromethyl-2-methyl-1,3-dioxolane) (S13-5) from Nitrokemia, which is known as safener for corn, "MG-838" (CAS Reg. No.: 133993-74-5) (2-propenyl 1-oxa-4-azaspiro[4.5]decane-4-carbodithioate) (S13-6) from Nitrokemia, "disulfoton" (O,O-diethyl S-2-ethylthioethyl phosphorodithioate) (S13-7), "dietholate" (O,O-diethyl O-phenyl phosphorothioate) (S13-8), "mephenate" (4-chlorophenyl methylcarbamate) (S13-9).

S14) Active compounds which, besides a herbicidal effect against harmful plants, also have a safener effect on crop plants such as rice, such as, for example, "dimepiperate" or "MY-93" (S-1-methyl-1-phenylethyl piperidine-1-carbothioate), which is known as safener for rice against molinate herbicide damage, "daimuron" or "SK 23" (1-(1-methyl-1-phenylethyl)-3-p-tolylurea), which is known as safener for rice against imazosulfuron herbicide damage, "cumyluron"="JC-940" (3-(2-chlorophenylmethyl)-1-(1-methyl-1-phenyl-ethypurea, see JP-A-60087254), which is known as safener for rice against damage by some herbicides, "methoxyphenone" or "NK 049" (3,3'-dimethyl-4-methoxybenzophenone), which is known as safener for rice against damage by some herbicides, "CSB" (1-bromo-4-(chloromethylsulfonyl)benzene) from Kumiai, (CAS Reg. No. 54091-06-4), which is known as safener for rice against damage by some herbicides.

S15) Active compounds which are primarily used as herbicides, but also have safener effect on crop plants, for example
(2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor-ethyl).

The herbicide/azole combinations according to the invention are, if appropriate in the presence of safeners, suitable for controlling harmful plants in crop plants, for example in economically important crops, such as cereals (for example wheat, barley, rye, oats, rice, corn, millet), sugar beet, sugar cane, oilseed rape, cotton and soybeans. Of particular interest here is the use in monocotyledonous crops such as cereals, for example wheat, barley, rye, oats, corn and millet.

If, in the context of this description, the short form of the "common name" of an active compound is used, this comprises in each case all customary derivatives, such as the esters and salts, and isomers, in particular optical isomers, especially the commercially available form or forms. If the "common name" refers to an ester or a salt, this in each case also comprises all other customary derivatives, such as other esters and salts, the free acids and neutral compounds, and isomers, in particular optical isomers, especially the commercially available form or forms. The given chemical compound names refer to at least one of the compounds embraced by the "common name", frequently to a preferred compound. In the case of sulfonamides such as sulfonylureas, salts also include salts formed by exchange of a hydrogen atom at the sulfonamide group for a cation.

The invention also comprises herbicide/azole combinations which, in addition to the components A) and B), also comprise one or more further agrochemically active compounds of a different structure, for example from the group of the herbicides, insecticides, fungicides, safeners or plant growth regulators. The preferred conditions outlined below in particular for combinations A)+B) according to the invention also apply primarily to these combinations if they comprise the combinations A)+B) according to the invention, and with respect to the combination A)+B) in question.

Of particular interest are herbicide/azole combinations according to the invention comprising the following compounds A)+B):

A1.1+B1, A1.2+B1, A2.1+B1, A2.2+B1, A3.1+B1, A3.2+B1, A4.1+B1, A4.2+B1, A5.1+B1, A5.2+B1, A6.1+B1, A6.2+B1, A7.1+B1, A7.2+B1, A8.1+B1, A8.2+B1, A9.1+B1, A9.2+B1, A10.1+B1, A10.2+B1, A11.1+B1, A11.2+B1, A12.1+B1, A12.2+B1, A13.1+B1, A13.2+B1, A14.1+B1, A14.2+B1, A15.1+B1, A15.2+B1, A16.1+B1, A16.2+B1, A17.1+B1, A17.2+B1, A18.1+B1, A18.2+B1, A19.1+B1, A19.2+B1, A20.1+B1, A20.2+B1, A21+B1, A22+B1, A23+B1, A24+B1, A25+B1, A26+B1, A27+B1;

A1.1+B2, A1.2+B2, A2.1+B2, A2.2+B2, A3.1+B2, A3.2+B2, A4.1+B2, A4.2+B2, A5.1+B2, A5.2+B2, A6.1+B2, A6.2+B2, A7.1+B2, A7.2+B2, A8.1+B2, A8.2+B2, A9.1+B2, A9.2+B2, A10.1+B2, A10.2+B2, A11.1+B2, A11.2+B2, A12.1+B2, A12.2+B2, A13.1+B2, A13.2+B2, A14.1+B2, A14.2+B2, A15.1+B2, A15.2+B2, A16.1+B2, A16.2+B2, A17.1+B2, A17.2+B2, A18.1+B2, A18.2+B2, A19.1+B2, A19.2+B2, A20.1+B2, A20.2+B2, A21+B2, A22+B2, A23+B2, A24+B2, A25+B2, A26+B2, A27+B3;

A1.1+B3, A1.2+B3, A2.1+B3, A2.2+B3, A3.1+B3, A3.2+B3, A4.1+B3, A4.2+B3, A5.1+B3, A5.2+B3, A6.1+B3, A6.2+B3, A7.1+B3, A7.2+B3, A8.1+B3, A8.2+B3, A9.1+B3, A9.2+B3, A10.1+B3, A10.2+B3, A11.1+B3, A11.2+B3, A12.1+B3, A12.2+B3, A13.1+B3, A13.2+B3, A14.1+B3, A14.2+B3, A15.1+B3, A15.2+B3, A16.1+B3, A16.2+B3, A17.1+B3, A17.2+B3, A18.1+B3, A18.2+B3, A19.1+

B3, A19.2+B3, A20.1+B3, A20.2+B3, A21+B3, A22+B3, A23+B3, A24+B3, A25+B3, A26+B3, A27+B3;

A1.1+B4, A1.2+B4, A2.1+B4, A2.2+B4, A3.1+B4, A3.2+B4, A4.1+B4, A4.2+B4, A5.1+B4, A5.2+B4, A6.1+B4, A6.2+B4, A7.1+B4, A7.2+B4, A8.1+B4, A8.2+B4, A9.1+B4, A9.2+B4, A10.1+B4, A10.2+B4, A11.1+B4, A11.2+B4, A12.1+B4, A12.2+B4, A13.1+B4, A13.2+B4, A14.1+B4, A14.2+B4, A15.1+B4, A15.2+B4, A16.1+B4, A16.2+B4, A17.1+B4, A17.2+B4, A18.1+B4, A18.2+B4, A19.1+B4, A19.2+B4, A20.1+B4, A20.2+B4, A21+B4, A22+B4, A23+B4, A24+B4, A25+B4, A26+B4, A27+B4;

A1.1+B5, A1.2+B5, A2.1+B5, A2.2+B5, A3.1+B5, A3.2+B5, A4.1+B5, A4.2+B5, A5.1+B5, A5.2+B5, A6.1+B5, A6.2+B5, A7.1+B5, A7.2+B5, A8.1+B5, A8.2+B5, A9.1+B5, A9.2+B5, A10.1+B5, A10.2+B5, A11.1+B5, A11.2+B5, A12.1+B5, A12.2+B5, A13.1+B5, A13.2+B5, A14.1+B5, A14.2+B5, A15.1+B5, A15.2+B5, A16.1+B5, A16.2+B5, A17.1+B5, A17.2+B5, A18.1+B5, A18.2+B5, A19.1+B5, A19.2+B5, A20.1+B5, A20.2+B5, A21+B5, A22+B5, A23+B5, A24+B5, A25+B5, A26+B5, A27+B5;

A1.1+B6, A1.2+B6, A2.1+B6, A2.2+B6, A3.1+B6, A3.2+B6, A4.1+B6, A4.2+B6, A5.1+B6, A5.2+B6, A6.1+B6, A6.2+B6, A7.1+B6, A7.2+B6, A8.1+B6, A8.2+B6, A9.1+B6, A9.2+B6, A10.1+B6, A10.2+B6, A11.1+B6, A11.2+B6, A12.1+B6, A12.2+B6, A13.1+B6, A13.2+B6, A14.1+B6, A14.2+B6, A15.1+B6, A15.2+B6, A16.1+B6, A16.2+B6, A17.1+B6, A17.2+B6, A18.1+B6, A18.2+B6, A19.1+B6, A19.2+B6, A20.1+B6, A20.2+B6, A21+B6, A22+B6, A23+B6, A24+B6, A25+B6, A26+B6, A27+B6;

A1.1+B7, A1.2+B7, A2.1+B7, A2.2+B7, A3.1+B7, A3.2+B7, A4.1+B7, A4.2+B7, A5.1+B7, A5.2+B7, A6.1+B7, A6.2+B7, A7.1+B7, A7.2+B7, A8.1+B7, A8.2+B7, A9.1+B7, A9.2+B7, A10.1+B7, A10.2+B7, A11.1+B7, A11.2+B7, A12.1+B7, A12.2+B7, A13.1+B7, A13.2+B7, A14.1+B7, A14.2+B7, A15.1+B7, A15.2+B7, A16.1+B7, A16.2+B7, A17.1+B7, A17.2+B7, A18.1+B7, A18.2+B7, A19.1+B7, A19.2+B7, A20.1+B7, A20.2+B7, A21+B7, A22+B7, A23+B7, A24+B7, A25+B7, A26+B7, A27+B7;

A1.1+B8, A1.2+B8, A2.1+B8, A2.2+B8, A3.1+B8, A3.2+B8, A4.1+B8, A4.2+B8, A5.1+B8, A5.2+B8, A6.1+B8, A6.2+B8, A7.1+B8, A7.2+B8, A8.1+B8, A8.2+B8, A9.1+B8, A9.2+B8, A10.1+B8, A10.2+B8, A11.1+B8, A11.2+B8, A12.1+B8, A12.2+B8, A13.1+B8, A13.2+B8, A14.1+B8, A14.2+B8, A15.1+B8, A15.2+B8, A16.1+B8, A16.2+B8, A17.1+B8, A17.2+B8, A18.1+B8, A18.2+B8, A19.1+B8, A19.2+B8, A20.1+B8, A20.2+B8, A21+B8, A22+B8, A23+B8, A24+B8, A25+B8, A26+B8, A27+B8;

A1.1+B9, A1.2+B9, A2.1+B9, A2.2+B9, A3.1+B9, A3.2+B9, A4.1+B9, A4.2+B9, A5.1+B9, A5.2+B9, A6.1+B9, A6.2+B9, A7.1+B9, A7.2+B9, A8.1+B9, A8.2+B9, A9.1+B9, A9.2+B9, A10.1+B9, A10.2+B9, A11.1+B9, A11.2+B9, A12.1+B9, A12.2+B9, A13.1+B9, A13.2+B9, A14.1+B9, A14.2+B9, A15.1+B9, A15.2+B9, A16.1+B9, A16.2+B9, A17.1+B9, A17.2+B9, A18.1+B9, A18.2+B9, A19.1+B9, A19.2+B9, A20.1+B9, A20.2+B9, A21+B9, A22+B9, A23+B9, A24+B9, A25+B9, A26+B9, A27+B9;

A1.1+B10, A1.2+B10, A2.1+B10, A2.2+B10, A3.1+B10, A3.2+B10, A4.1+B10, A4.2+B10, A5.1+B10, A5.2+B10, A6.1+B10, A6.2+B10, A7.1+B10, A7.2+B10, A8.1+B10, A8.2+B10, A9.1+B10, A9.2+B10, A10.1+B10, A10.2+B10, A11.1+B10, A11.2+B10, A12.1+B10, A12.2+B10, A13.1+B10, A13.2+B10, A14.1+B10, A14.2+B10, A15.1+B10, A15.2+B10, A16.1+B10, A16.2+B10, A17.1+B10, A17.2+B10, A18.1+B10, A18.2+B10, A19.1+B10, A19.2+B10, A20.1+B10, A20.2+B10, A21+B10, A22+B10, A23+B10, A24+B10, A25+B10, A26+B10, A27+B10;

A1.1+B11, A1.2+B11, A2.1+B11, A2.2+B11, A3.1+B11, A3.2+B11, A4.1+B11, A4.2+B11, A5.1+B11, A5.2+B11, A6.1+B11, A6.2+B11, A7.1+B11, A7.2+B11, A8.1+B11, A8.2+B11, A9.1+B11, A9.2+B11, A10.1+B11, A10.2+B11, A11.1+B11, A11.2+B11, A12.1+B11, A12.2+B11, A13.1+B11, A13.2+B11, A14.1+B11, A14.2+B11, A15.1+B11, A15.2+B11, A16.1+B11, A16.2+B11, A17.1+B11, A17.2+B11, A18.1+B11, A18.2+B11, A19.1+B11, A19.2+B11, A20.1+B11, A20.2+B11, A21+B11, A22+B11, A23+B11, A24+B11, A25+B11, A26+B11, A27+B11;

A1.1+B12, A1.2+B12, A2.1+B12, A2.2+B12, A3.1+B12, A3.2+B12, A4.1+B12, A4.2+B12, A5.1+B12, A5.2+B12, A6.1+B12, A6.2+B12, A7.1+B12, A7.2+B12, A8.1+B12, A8.2+B12, A9.1+B12, A9.2+B12, A10.1+B12, A10.2+B12, A11.1+B12, A11.2+B12, A12.1+B12, A12.2+B12, A13.1+B12, A13.2+B12, A14.1+B12, A14.2+B12, A15.1+B12, A15.2+B12, A16.1+B12, A16.2+B12, A17.1+B12, A17.2+B12, A18.1+B12, A18.2+B12, A19.1+B12, A19.2+B12, A20.1+B12, A20.2+B12, A21+B12, A22+B12, A23+B12, A24+B12, A25+B12, A26+B12, A27+B12;

A1.1+B13, A1.2+B13, A2.1+B13, A2.2+B13, A3.1+B13, A3.2+B13, A4.1+B13, A4.2+B13, A5.1+B13, A5.2+B13, A6.1+B13, A6.2+B13, A7.1+B13, A7.2+B13, A8.1+B13, A8.2+B13, A9.1+B13, A9.2+B13, A10.1+B13, A10.2+B13, A11.1+B13, A11.2+B13, A12.1+B13, A12.2+B13, A13.1+B13, A13.2+B13, A14.1+B13, A14.2+B13, A15.1+B13, A15.2+B13, A16.1+B13, A16.2+B13, A17.1+B13, A17.2+B13, A18.1+B13, A18.2+B13, A19.1+B13, A19.2+B13, A20.1+B13, A20.2+B13, A21+B13, A22+B13, A23+B13, A24+B13, A25+B13, A26+B13, A27+B13;

A1.1+B14, A1.2+B14, A2.1+B14, A2.2+B14, A3.1+B14, A3.2+B14, A4.1+B14, A4.2+B14, A5.1+B14, A5.2+B14, A6.1+B14, A6.2+B14, A7.1+B14, A7.2+B14, A8.1+B14, A8.2+B14, A9.1+B14, A9.2+B14, A10.1+B14, A10.2+B14, A11.1+B14, A11.2+B14, A12.1+B14, A12.2+B14, A13.1+B14, A13.2+B14, A14.1+B14, A14.2+B14, A15.1+B14, A15.2+B14, A16.1+B14, A16.2+B14, A17.1+B14, A17.2+B14, A18.1+B14, A18.2+B14, A19.1+B14, A19.2+B14, A20.1+B14, A20.2+B14, A21+B14, A22+B14, A23+B14, A24+B14, A25+B14, A26+B14, A27+B14;

A1.1+B15, A1.2+B15, A2.1+B15, A2.2+B15, A3.1+B15, A3.2+B15, A4.1+B15, A4.2+B15, A5.1+B15, A5.2+B15, A6.1+B15, A6.2+B15, A7.1+B15, A7.2+B15, A8.1+B15, A8.2+B15, A9.1+B15, A9.2+B15, A10.1+B15, A10.2+B15, A11.1+B15, A11.2+B15, A12.1+B15, A12.2+B15, A13.1+B15, A13.2+B15, A14.1+B15, A14.2+B15, A15.1+B15, A15.2+B15, A16.1+B15, A16.2+B15, A17.1+B15, A17.2+B15, A18.1+B15, A18.2+B15, A19.1+B15, A19.2+B15, A20.1+B15, A20.2+B15, A21+B15, A22+B15, A23+B15, A24+B15, A25+B15, A26+B15, A27+B15;

A1.1+B16, A1.2+B16, A2.1+B16, A2.2+B16, A3.1+B16, A3.2+B16, A4.1+B16, A4.2+B16, A5.1+B16, A5.2+B16, A6.1+B16, A6.2+B16, A7.1+B16, A7.2+B16, A8.1+B16, A8.2+B16, A9.1+B16, A9.2+B16, A10.1+B16, A10.2+B16, A11.1+B16, A11.2+B16, A12.1+B16, A12.2+B16, A13.1+B16, A13.2+B16, A14.1+B16, A14.2+B16, A15.1+B16, A15.2+B16, A16.1+B16, A16.2+B16, A17.1+B16, A17.2+B16, A18.1+B16, A18.2+B16, A19.1+B16, A19.2+B16, A20.1+B16, A20.2+B16, A21+B16, A22+B16, A23+B16, A24+B16, A25+B16, A26+B16, A27+B16;

A1.1+B17, A1.2+B17, A2.1+B17, A2.2+B17, A3.1+B17, A3.2+B17, A4.1+B17, A4.2+B17, A5.1+B17, A5.2+B17, A6.1+B17, A6.2+B17, A7.1+B17, A7.2+B17, A8.1+B17, A8.2+B17, A9.1+B17, A9.2+B17, A10.1+B17, A10.2+B17, A11.1+B17, A11.2+B17, A12.1+B17, A12.2+B17, A13.1+B17, A13.2+B17, A14.1+B17, A14.2+B17, A15.1+B17, A15.2+B17, A16.1+B17, A16.2+B17, A17.1+B17, A17.2+B17, A18.1+B17, A18.2+B17, A19.1+B17, A19.2+B17, A20.1+B17, A20.2+B17, A21+B17, A22+B17, A23+B17, A24+B17, A25+B17, A26+B17, A27+B17;

A1.1+B18, A1.2+B18, A2.1+B18, A2.2+B18, A3.1+B18, A3.2+B18, A4.1+B18, A4.2+B18, A5.1+B18, A5.2+B18, A6.1+B18, A6.2+B18, A7.1+B18, A7.2+B18, A8.1+B18, A8.2+B18, A9.1+B18, A9.2+B18, A10.1+B18, A10.2+B18, A11.1+B18, A11.2+B18, A12.1+B18, A12.2+B18, A13.1+B18, A13.2+B18, A14.1+B18, A14.2+B18, A15.1+B18, A15.2+B18, A16.1+B18, A16.2+B18, A17.1+B18, A17.2+B18, A18.1+B18, A18.2+B18, A19.1+B18, A19.2+B18, A20.1+B18, A20.2+B18, A21+B18, A22+B18, A23+B18, A24+B18, A25+B18, A26+B18, A27+B18;

A1.1+B19, A1.2+B19, A2.1+B19, A2.2+B19, A3.1+B19, A3.2+B19, A4.1+B19, A4.2+B19, A5.1+B19, A5.2+B19, A6.1+B19, A6.2+B19, A7.1+B19, A7.2+B19, A8.1+B19, A8.2+B19, A9.1+B19, A9.2+B19, A10.1+B19, A10.2+B19, A11.1+B19, A11.2+B19, A12.1+B19, A12.2+B19, A13.1+B19, A13.2+B19, A14.1+B19, A14.2+B19, A15.1+B19, A15.2+B19, A16.1+B19, A16.2+B19, A17.1+B19, A17.2+B19, A18.1+B19, A18.2+B19, A19.1+B19, A19.2+B19, A20.1+B19, A20.2+B19, A21+B19, A22+B19, A23+B19, A24+B19, A25+B19, A26+B19, A27+B19;

A1.1+B20, A1.2+B20, A2.1+B20, A2.2+B20, A3.1+B20, A3.2+B20, A4.1+B20, A4.2+B20, A5.1+B20, A5.2+B20, A6.1+B20, A6.2+B20, A7.1+B20, A7.2+B20, A8.1+B20, A8.2+B20, A9.1+B20, A9.2+B20, A10.1+B20, A10.2+B20, A11.1+B20, A11.2+B20, A12.1+B20, A12.2+B20, A13.1+B20, A13.2+B20, A14.1+B20, A14.2+B20, A15.1+B20, A15.2+B20, A16.1+B20, A16.2+B20, A17.1+B20, A17.2+B20, A18.1+B20, A18.2+B20, A19.1+B20, A19.2+B20, A20.1+B20, A20.2+B20, A21+B20, A22+B20, A23+B20, A24+B20, A25+B20, A26+B20, A27+B20;

A1.1+B21, A1.2+B21, A2.1+B21, A2.2+B21, A3.1+B21, A3.2+B21, A4.1+B21, A4.2+B21, A5.1+B21, A5.2+B21, A6.1+B21, A6.2+B21, A7.1+B21, A7.2+B21, A8.1+B21, A8.2+B21, A9.1+B21, A9.2+B21, A10.1+B21, A10.2+B21, A11.1+B21, A11.2+B21, A12.1+B21, A12.2+B21, A13.1+B21, A13.2+B21, A14.1+B21, A14.2+B21, A15.1+B21, A15.2+B21, A16.1+B21, A16.2+B21, A17.1+B21, A17.2+B21, A18.1+B21, A18.2+B21, A19.1+B21, A19.2+B21, A20.1+B21, A20.2+B21, A21+B21, A22+B21, A23+B21, A24+B21, A25+B21, A26+B21, A27+B21;

A1.1+B22, A1.2+B22, A2.1+B22, A2.2+B22, A3.1+B22, A3.2+B22, A4.1+B22, A4.2+B22, A5.1+B22, A5.2+B22, A6.1+B22, A6.2+B22, A7.1+B22, A7.2+B22, A8.1+B22, A8.2+B22, A9.1+B22, A9.2+B22, A10.1+B22, A10.2+B22, A11.1+B22, A11.2+B22, A12.1+B22, A12.2+B22, A13.1+B22, A13.2+B22, A14.1+B22, A14.2+B22, A15.1+B22, A15.2+B22, A16.1+B22, A16.2+B22, A17.1+B22, A17.2+B22, A18.1+B22, A18.2+B22, A19.1+B22, A19.2+B22, A20.1+B22, A20.2+B22, A21+B22, A22+B22, A23+B22, A24+B22, A25+B22, A26+B22, A27+B22;

A1.1+B23, A1.2+B23, A2.1+B23, A2.2+B23, A3.1+B23, A3.2+B23, A4.1+B23, A4.2+B23, A5.1+B23, A5.2+B23, A6.1+B23, A6.2+B23, A7.1+B23, A7.2+B23, A8.1+B23, A8.2+B23, A9.1+B23, A9.2+B23, A10.1+B23, A10.2+B23, A11.1+B23, A11.2+B23, A12.1+B23, A12.2+B23, A13.1+B23, A13.2+B23, A14.1+B23, A14.2+B23, A15.1+B23, A15.2+B23, A16.1+B23, A16.2+B23, A17.1+B23, A17.2+B23, A18.1+B23, A18.2+B23, A19.1+B23, A19.2+B23, A20.1+B23, A20.2+B23, A21+B23, A22+B23, A23+B23, A24+B23, A25+B23, A26+B23, A27+B23;

A1.1+B24, A1.2+B24, A2.1+B24, A2.2+B24, A3.1+B24, A3.2+B24, A4.1+B24, A4.2+B24, A5.1+B24, A5.2+B24, A6.1+B24, A6.2+B24, A7.1+B24, A7.2+B24, A8.1+B24, A8.2+B24, A9.1+B24, A9.2+B24, A10.1+B24, A10.2+B24, A11.1+B24, A11.2+B24, A12.1+B24, A12.2+B24, A13.1+B24, A13.2+B24, A14.1+B24, A14.2+B24, A15.1+B24, A15.2+B24, A16.1+B24, A16.2+B24, A17.1+B24, A17.2+B24, A18.1+B24, A18.2+B24, A19.1+B24, A19.2+B24, A20.1+B24, A20.2+B24, A21+B24, A22+B24, A23+B24, A24+B24, A25+B24, A26+B24, A27+B24;

A1.1+B25, A1.2+B25, A2.1+B25, A2.2+B25, A3.1+B25, A3.2+B25, A4.1+B25, A4.2+B25, A5.1+B25, A5.2+B25, A6.1+B25, A6.2+B25, A7.1+B25, A7.2+B25, A8.1+B25, A8.2+B25, A9.1+B25, A9.2+B25, A10.1+B25, A10.2+B25, A11.1+B25, A11.2+B25, A12.1+B25, A12.2+B25, A13.1+B25, A13.2+B25, A14.1+B25, A14.2+B25, A15.1+B25, A15.2+B25, A16.1+B25, A16.2+B25, A17.1+B25, A17.2+B25, A18.1+B25, A18.2+B25, A19.1+B25, A19.2+B25, A20.1+B25, A20.2+B25, A21+B25, A22+B25, A23+B25, A24+B25, A25+B25, A26+B25, A27+B25;

A1.1+B26, A1.2+B26, A2.1+B26, A2.2+B26, A3.1+B26, A3.2+B26, A4.1+B26, A4.2+B26, A5.1+B26, A5.2+B26, A6.1+B26, A6.2+B26, A7.1+B26, A7.2+B26, A8.1+B26, A8.2+B26, A9.1+B26, A9.2+B26, A10.1+B26, A10.2+B26, A11.1+B26, A11.2+B26, A12.1+B26, A12.2+B26, A13.1+B26, A13.2+B26, A14.1+B26, A14.2+B26, A15.1+B26, A15.2+B26, A16.1+B26, A16.2+B26, A17.1+B26, A17.2+B26, A18.1+B26, A18.2+B26, A19.1+B26, A19.2+B26, A20.1+B26, A20.2+B26, A21+B26, A22+B26, A23+B26, A24+B26, A25+B26, A26+B26, A27+B26;

A1.1+B27, A1.2+B27, A2.1+B27, A2.2+B27, A3.1+B27, A3.2+B27, A4.1+B27, A4.2+B27, A5.1+B27, A5.2+B27, A6.1+B27, A6.2+B27, A7.1+B27, A7.2+B27, A8.1+B27, A8.2+B27, A9.1+B27, A9.2+B27, A10.1+B27, A10.2+B27, A11.1+B27, A11.2+B27, A12.1+B27, A12.2+B27, A13.1+B27, A13.2+B27, A14.1+B27, A14.2+B27, A15.1+B27, A15.2+B27, A16.1+B27, A16.2+B27, A17.1+B27, A17.2+B27, A18.1+B27, A18.2+B27, A19.1+B27, A19.2+B27, A20.1+B27, A20.2+B27, A21+B27, A22+B27, A23+B27, A24+B27, A25+B27, A26+B27, A27+B27;

A1.1+B28, A1.2+B28, A2.1+B28, A2.2+B28, A3.1+B28, A3.2+B28, A4.1+B28, A4.2+B28, A5.1+B28, A5.2+B28, A6.1+B28, A6.2+B28, A7.1+B28, A7.2+B28, A8.1+B28, A8.2+B28, A9.1+B28, A9.2+B28, A10.1+B28, A10.2+B28, A11.1+B28, A11.2+B28, A12.1+B28, A12.2+B28, A13.1+B28, A13.2+B28, A14.1+B28, A14.2+B28, A15.1+B28, A15.2+B28, A16.1+B28, A16.2+B28, A17.1+B28, A17.2+B28, A18.1+B28, A18.2+B28, A19.1+B28, A19.2+B28, A20.1+B28, A20.2+B28, A21+B28, A22+B28, A23+B28, A24+B28, A25+B28, A26+B28, A27+B28;

A1.1+B29, A1.2+B29, A2.1+B29, A2.2+B29, A3.1+B29, A3.2+B29, A4.1+B29, A4.2+B29, A5.1+B29, A5.2+B29, A6.1+B29, A6.2+B29, A7.1+B29, A7.2+B29, A8.1+B29, A8.2+B29, A9.1+B29, A9.2+B29, A10.1+B29, A10.2+B29, A11.1+B29, A11.2+B29, A12.1+B29, A12.2+B29, A13.1+B29, A13.2+B29, A14.1+B29, A14.2+B29, A15.1+B29, A15.2+B29, A16.1+B29, A16.2+B29, A17.1+B29, A17.2+B29, A18.1+B29, A18.2+B29, A19.1+B29, A19.2+B29, A20.1+B29, A20.2+B29, A21+B1, A22+B1, A23+B1, A24+B1, A25+B1, A26+B1, A27+B1;

A1.1+B30, A1.2+B30, A2.1+B30, A2.2+B30, A3.1+B30, A3.2+B30, A4.1+B30, A4.2+B30, A5.1+B30, A5.2+B30, A6.1+B30, A6.2+B30, A7.1+B30, A7.2+B30, A8.1+B30, A8.2+B30, A9.1+B30, A9.2+B30, A10.1+B30, A10.2+B30, A11.1+B30, A11.2+B30, A12.1+B30, A12.2+B30, A13.1+B30, A13.2+B30, A14.1+B30, A14.2+B30, A15.1+B30, A15.2+B30, A16.1+B30, A16.2+B30, A17.1+B30, A17.2+B30, A18.1+B30, A18.2+B30, A19.1+B30, A19.2+B30, A20.1+B30, A20.2+B30, A21+B30, A22+B30, A23+B30, A24+B30, A25+B30, A26+B30, A27+B30;

A1.1+B31, A1.2+B31, A2.1+B31, A2.2+B31, A3.1+B31, A3.2+B31, A4.1+B31, A4.2+B31, A5.1+B31, A5.2+B31, A6.1+B31, A6.2+B31, A7.1+B31, A7.2+B31, A8.1+B31, A8.2+B31, A9.1+B31, A9.2+B31, A10.1+B31, A10.2+B31, A11.1+B31, A11.2+B31, A12.1+B31, A12.2+B31, A13.1+B31, A13.2+B31, A14.1+B31, A14.2+B31, A15.1+B31, A15.2+B31, A16.1+B31, A16.2+B31, A17.1+B31, A17.2+B31, A18.1+B31, A18.2+B31, A19.1+B31, A19.2+B31, A20.1+B31, A20.2+B31, A21+B31, A22+B31, A23+B31, A24+B31, A25+B31, A26+B31, A27+B31;

A1.1+B32, A1.2+B32, A2.1+B32, A2.2+B32, A3.1+B32, A3.2+B32, A4.1+B32, A4.2+B32, A5.1+B32, A5.2+B32, A6.1+B32, A6.2+B32, A7.1+B32, A7.2+B32, A8.1+B32, A8.2+B32, A9.1+B32, A9.2+B32, A10.1+B32, A10.2+B32, A11.1+B32, A11.2+B32, A12.1+B32, A12.2+B32, A13.1+B32, A13.2+B32, A14.1+B32, A14.2+B32, A15.1+B32, A15.2+B32, A16.1+B32, A16.2+B32, A17.1+B32, A17.2+B32, A18.1+B32, A18.2+B32, A19.1+B32, A19.2+B32, A20.1+B32, A20.2+B32, A21+B32, A22+B32, A23+B32, A24+B32, A25+B32, A26+B32, A27+B32;

A1.1+B33, A1.2+B33, A2.1+B33, A2.2+B33, A3.1+B33, A3.2+B33, A4.1+B33, A4.2+B33, A5.1+B33, A5.2+B33, A6.1+B33, A6.2+B33, A7.1+B33, A7.2+B33, A8.1+B33, A8.2+B33, A9.1+B33, A9.2+B33, A10.1+B33, A10.2+B33, A11.1+B33, A11.2+B33, A12.1+B33, A12.2+B33, A13.1+B33, A13.2+B33, A14.1+B33, A14.2+B33, A15.1+B33, A15.2+B33, A16.1+B33, A16.2+B33, A17.1+B33, A17.2+B33, A18.1+B33, A18.2+B33, A19.1+B33, A19.2+B33, A20.1+B33, A20.2+B33, A21+B33, A22+B33, A23+B33, A24+B33, A25+B33, A26+B33, A27+B33;

A1.1+B34, A1.2+B34, A2.1+B34, A2.2+B34, A3.1+B34, A3.2+B34, A4.1+B34, A4.2+B34, A5.1+B34, A5.2+B34, A6.1+B34, A6.2+B34, A7.1+B34, A7.2+B34, A8.1+B34, A8.2+B34, A9.1+B34, A9.2+B34, A10.1+B34, A10.2+B34, A11.1+B34, A11.2+B34, A12.1+B34, A12.2+B34, A13.1+B34, A13.2+B34, A14.1+B34, A14.2+B34, A15.1+B34, A15.2+B34, A16.1+B34, A16.2+B34, A17.1+B34, A17.2+B34, A18.1+B34, A18.2+B34, A19.1+B34, A19.2+B34, A20.1+B34, A20.2+B34, A21+B34, A22+B34, A23+B34, A24+B34, A25+B34, A26+B34, A27+B34;

A1.1+B35, A1.2+B35, A2.1+B35, A2.2+B35, A3.1+B35, A3.2+B35, A4.1+B35, A4.2+B35, A5.1+B35, A5.2+B35, A6.1+B35, A6.2+B35, A7.1+B35, A7.2+B35, A8.1+B35, A8.2+B35, A9.1+B35, A9.2+B35, A10.1+B35, A10.2+B35, A11.1+B35, A11.2+B35, A12.1+B35, A12.2+B35, A13.1+B35, A13.2+B35, A14.1+B35, A14.2+B35, A15.1+B35, A15.2+B35, A16.1+B35, A16.2+B35, A17.1+B35, A17.2+B35, A18.1+B35, A18.2+B35, A19.1+B35, A19.2+B35, A20.1+B35, A20.2+B35, A21+B35, A22+B35, A23+B35, A24+B35, A25+B35, A26+B35, A27+B35;

In addition, each of the active compound combinations mentioned above may also comprise a safener, in particular a safener from the group consisting of mefenpyr-diethyl (S1-1), isoxadifen-ethyl (S1-11), cloquintocet-methyl (S2-1) and cyprosulfamide (S4-1).

It may be expedient to combine one or more active compounds A) with one or more active compounds B), or a plurality of active compounds A) with one or more active compounds B). Furthermore, the combinations according to the invention may be applied together with other agrochemically active compounds, for example from the group of the safeners, fungicides, herbicides, insecticides and plant growth regulators, and also with additives customary in crop protection, such as tackifiers, wetting agents, dispersants, emulsifiers, preservatives, antifreeze agents and solvents, fillers and carriers, antifoams, evaporation inhibitors or pH— or viscosity-modifying agents.

The combinations according to the invention have excellent herbicidal activity against a broad spectrum of economically important mono- and dicotyledonous harmful plants. Difficult-to-control perennial weeds which produce shoots from rhizomes, root stocks or other perennial organs are also well controlled by the active compounds. Here, the substances can be applied, for example, by the pre-sowing method, the pre-emergence method and/or the post-emergence method, for example jointly or separately. Post-emergence application is preferred.

Specific mention may be made of some representatives of the mono- and dicotyledonous weed flora which can be controlled by the combinations according to the invention; however, this list is not to be understood as meaning a limitation to certain species.

Examples of weed species which are controlled efficiently are, from amongst the monocotyledonous weed species, *Avena* spp., *Alopecurus* spp., *Brachiaria* spp., *Digitaria* spp., *Lolium* spp., *Echinochloa* spp., *Panicum* spp., *Phalaris* spp., *Poa* spp., *Setaria* spp. and also *Bromus* spp. such as *Bromus catharticus, Bromus secalinus, Bromus erectus, Bromus tectorum* and *Bromus japonicus* and *Cyperus* species from the annual group, and, among the perennial species, *Agropyron, Cynodon, Imperata* and *Sorghum* and also perennial *Cyperus* species.

In the case of dicotyledonous weed species, the spectrum of action extends to genera such as, for example, *Abutilon* spp., *Amaranthus* spp., *Chenopodium* spp., *Chrysanthemum* spp., *Galium* spp. such as *Galium aparine, Ipomoea* spp., *Kochia* spp., *Lamium* spp., *Matricaria* spp., *Pharbitis* spp., *Polygonum* spp., *Sida* spp., *Sinapis* spp., *Solanum* spp., *Stellaria* spp., *Veronica* spp. and *Viola* spp., *Xanthium* spp., among the annuals, and *Convolvulus, Cirsium, Rumex* and *Artemisia* in the case of the perennial weeds.

If the combinations according to the invention are applied to the soil surface before or during germination, the weed seedlings are inhibited or prevented completely from emerging or else the weeds grow until they have reached the cotyledon stage, but then their growth stops, and, eventually, after three to four weeks have elapsed, they die completely.

If the active compounds are applied post-emergence to the green parts of the plants, growth likewise stops rapidly a very short time after the treatment, and the weed plants remain at the growth stage of the point of time of application, or they die completely after a certain time, so that in this manner competition by the weeds, which is harmful to the crop plants, is eliminated very early and in a sustained manner.

The combinations according to the invention are distinguished by a rapidly commencing and long-lasting herbicidal action. As a rule, the rainfastness of the active compounds in the combinations according to the invention is favorable. A particular advantage is that the dosages used in the combinations and the effective dosages of active compounds A) and B) can be adjusted to such a low level that their soil action is optimally low. This does not only allow them to be employed in sensitive crops in the first place, but ground water contaminations are virtually avoided. The combination according to the invention of active compounds allows the required active compound application rates to be reduced considerably, which may lead, for example, to improved replant behavior.

When the active compounds A) and B) are applied in combination, in a preferred embodiment superadditive (=synergistic) herbicidal effects are observed. Here, the herbicidal activity of the combination is higher than the expected sum of the activities of the individual active compounds employed. The synergistic effects allow the application rate to be reduced, a broader spectrum of broad-leaved weeds and weed grasses to be controlled, a more rapid onset of the herbicidal action, a longer persistency, a better control of the harmful plants with only one or a few applications and a widening of the application period possible.

The abovementioned properties and advantages are of benefit in weed control practice to keep agricultural crops free of unwanted competing plants, and thus to ensure and/or increase yield levels from the qualitative and quantitative angles. With respect to the described properties, the prior art is considerably surpassed by these novel combinations.

Although the combinations according to the invention have an excellent herbicidal activity against monocotyledonous and dicotyledonous weeds, the crop plants are not damaged at all, or only to a negligible extent.

In addition, the combinations according to the invention have in some cases outstanding growth-regulating properties in crop plants. They engage in the plant metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting unwanted vegetative growth without destroying the plants in the process. Inhibiting the vegetative growth plays an important role in many monocotyledonous and dicotyledonous crops since yield losses as a result of lodging can be reduced, or prevented completely, hereby.

By virtue of their herbicidal and plant growth-regulatory properties, the combinations according to the invention can also be employed for controlling harmful plants in crop plants which are genetically modified or have been obtained by mutation/selection. In general, these crop plants are distinguished by specific advantageous properties, such as resistances to herbicidal compositions or by resistances to plant diseases or the causative organisms of plant diseases such as certain insects or microorganisms, such as fungi, bacteria or viruses. Other specific characteristics relate, for example, to the harvested material with regard to quantity, quality, storeability, composition and specific constituents. Thus, for example, transgenic plants are known whose starch content is increased, or whose starch quality is altered, or those where the harvested material has a different fatty acid composition.

Conventional methods of generating novel plants which have modified properties in comparison to plants occurring to date consist, for example, in traditional breeding methods and the generation of mutants (see, for example, U.S. Pat. No. 5,162,602; U.S. Pat. No. 4,761,373; U.S. Pat. No. 4,443,971). Alternatively, novel plants with altered properties can be generated with the aid of recombinant methods (see, for example, EP-A-0221044, EP-A-0131624). For example, the following have been described in several cases:

the modification, by recombinant technology, of crop plants with the aim of modifying the starch synthesized in the plants (for example WO 92/11376, WO 92/14827, WO 91/19806), transgenic crop plants which exhibit resistances to other herbicides, for example to sulfonylureas (EP-A-0257993, U.S. Pat. No. 5,013,659), transgenic crop plants with the capability of producing *Bacillus thuringiensis* toxins (Bt toxins), which make the plants resistant to certain pests (EP-A-0142924, EP-A-0193259), transgenic crop plants with a modified fatty acid composition (WO 91/13972).

A large number of techniques in molecular biology are known in principle with the aid of which novel transgenic plants with modified properties can be generated; see, for example, Sambrook et al., 1989, Molecular Cloning, A Laboratory Manual, $2^{nd}$ Edition, Cold Spring Harbor Laboratory Press, Cold Spring Harbor, N.Y.; or Winnacker "Gene and Klone", VCH Weinheim $2^{nd}$ Edition 1996 or Christou, "Trends in Plant Science" 1 (1996) 423-431).

To carry out such recombinant manipulations, nucleic acid molecules which allow mutagenesis or sequence changes by recombination of DNA sequences can be introduced into plasmids. For example, base substitutions can be carried out, part-sequences can be removed, or natural or synthetic sequences may be added with the aid of the standard methods mentioned above. To connect the DNA fragments to each other, adapters or linkers may be added to the fragments.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the above-mentioned gene product.

To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to link the coding region with DNA sequences which ensure localization in a particular compartment. Such sequences are known to the person skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated by known techniques to give rise to entire plants. In principle, the transgenic plants can be plants of any desired plant species, i.e. not only monocotyledonous, but also dicotyledonous, plants. Thus, transgenic plants can be obtained whose properties are altered by overexpression, suppression or inhibition of homologous (=natural) genes or gene sequences or the expression of heterologous (=foreign) genes or gene sequences.

Furthermore, the present invention also provides a method for controlling unwanted vegetation, preferably in crop plants such as cereals (for example wheat, barley, rye, oats, rice, corn, millet), sugar beet, sugar cane, oilseed rape, cotton and soybean, particularly preferably in monocotyledonous crops such as cereals, for example wheat, barley, rye, oats, rice, corn and millet, which method comprises applying one or more active compounds A) and one or more active compounds B) jointly or separately to the plants, parts of plants, plant seed or the area on which the plants grow, for example the area under cultivation.

The crop plants may also be genetically modified or obtained by mutation/selection and are preferably tolerant to acetolactate synthase (ALS) inhibitors.

The invention also provides the use of the combinations according to the invention for controlling harmful plants, preferably in crop plants.

The combinations according to the invention can also be employed non-selectively for controlling unwanted vegetation, for example in plantation crops, on roadsides, squares, industrial sites or railway tracks.

The combinations according to the invention can be present both as mixed formulations of components A) and B), if appropriate with further agrochemically active compounds and/or additives which are then applied in a customary manner diluted with water, or can be prepared as so-called tank mixes by joint dilution of the separately formulated or partially separately formulated components with water.

The components A) and B) or their combinations can be formulated in various ways according to which biological and/or physicochemical parameters are required. Examples of general formulation options are: wettable powders (WP), water-soluble concentrates, emulsifiable concentrates (EC), aqueous solutions (SL), emulsions (EW), such as oil-in-water and water-in-oil emulsions, sprayable solutions or emulsions, suspension concentrates (SC or FS), oil-based dispersions (OD) or water-based dispersions, suspoemulsions (SE), dusts (DP), seed-dressing compositions, granules, for example for broadcasting and soil application or water-dispersible granules (WDG) or water-emulsifiable granules (WEG), ULV formulations, microcapsules or waxes.

The individual types of formulation are known in principle and are described, for example, in: Winnacker-Küchler, "Chemische Technologie" [Chemical technology], Volume 7, C. Hanser Verlag Munich, 4th Ed. 1986, van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1950; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesellschaft, Stuttgart 1976; Winnacker-Küchler, "Chemische Technologie" [Chemical Technology], Volume 7, C. Hanser Verlag Munich, 4th Edition 1986.

Based on these formulations, it is also possible to produce combinations with other agrochemically active compounds, such as other herbicides, fungicides, insecticides, and also with safeners, fertilizers and/or growth regulators, for example in the form of a finished formulation or as a tank mix.

Wettable powders are preparations which are uniformly dispersible in water and which contain, in addition to the active compound and as well as a diluent or inert substance, surfactants of ionic or nonionic type (wetting agents, dispersants), for example polyethoxylated alkyl phenols, polyethoxylated fatty alcohols, polyethoxylated fatty amines, alkanesulfonates, alkylbenzenesulfonates, sodium lignosulfonate, sodium 2,2'-dinaphthylmethane-6,6'-disulfonate, sodium dibutylnaphthalene-sulfonate or else sodium oleoylmethyltaurinate.

Emulsifiable concentrates are prepared by dissolving the active compound in an organic solvent, for example butanol, cyclohexanone, dimethylformamide, xylene or else relatively high-boiling aromatics or hydrocarbons with addition of one or more ionic or nonionic surfactants (emulsifiers). The emulsifiers used may, for example, be: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan fatty acid esters, polyoxyethylene sorbitan fatty acid esters or polyoxyethylene sorbitol esters.

Dusts are obtained by grinding the active compound with finely distributed solid substances, for example talc, natural clays, such as kaolin, bentonite and pyrophyllite, or diatomaceous earth.

Suspension concentrates (SC) may be water- or oil-based. They may be prepared, for example, by wet grinding by means of commercial bead mills and optional addition of further surfactants as have, for example, already been listed above for the other formulation types.

Emulsions, for example oil-in-water emulsions (EW), can be prepared, for example, by means of stirrers, colloid mills and/or static mixers using aqueous organic solvents and optionally further surfactants, as have, for example, already been listed above for the other formulation types.

Granules can be prepared either by spraying the active compound onto granular inert material capable of adsorption or by applying active compound concentrates to the surface of carrier substances, such as sand, kaolinites or granular inert material, by means of adhesives, for example polyvinyl alcohol, sodium polyacrylate or mineral oils. Suitable active compounds can also be granulated in the manner customary for the preparation of fertilizer granules—if desired as a mixture with fertilizers. Water-dispersible granules are prepared generally by the customary processes such as spray-drying, fluidized bed granulation, pan granulation, mixing with high-speed mixers and extrusion without solid inert material. For the preparation of pan, fluidized bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, p. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations generally comprise from 0.1 to 99% by weight, in particular from 2 to 95% by weight, of active compounds A) and/or B), the following concentrations being customary, depending on the type of formulation:

In wettable powders, the active compound concentration is, for example, from about 10 to 95% by weight, the remainder to 100% by weight consisting of customary formulation components. In the case of emulsifiable concentrates, the active compound concentration can be, for example, from 5 to 80% by weight. In most cases, formulations in the form of dusts comprise from 5 to 20% by weight of active compound, sprayable solutions comprise about 0.2 to 25% by weight of active compound. In the case of granules such as dispersible granules, the active compound content depends partially on whether the active compound is present in liquid or solid form and on which granulation auxiliaries and fillers are used. In water-dispersible granules the content is generally between 10 and 90% by weight.

In addition, the active compound formulations mentioned optionally comprise the respective customary additives, such as adhesives, wetting agents, dispersants, emulsifiers, preservatives, antifreeze agents and solvents, fillers, colorants and carriers, antifoams, evaporation inhibitors and pH- and viscosity-modifying agents.

The herbicidal action of the herbicide/azole combinations according to the invention can be improved, for example, by surfactants, preferably by wetting agents from the group of the fatty alcohol polyglycol ethers. The fatty alcohol polyglycol ethers preferably comprise 10-18 carbon atoms in the fatty alcohol radical and 2-20 ethylene oxide units in the polyglycol ether moiety. The fatty alcohol polyglycol ethers may be present in nonionic form, or ionic form, for example in the form of fatty alcohol polyglycol ether sulfates, which may be used, for example, as alkali metal salts (for example sodium salts and potassium salts) or ammonium salts, or even as alkaline earth metal salts, such as magnesium salts, such as $C_{12}/C_{14}$-fatty alcohol diglycol ether sulfate sodium (Genapol® LRO, Clariant GmbH); see, for example, EP-A-0476555, EP-A-0048436, EP-A-0336151 or U.S. Pat. No. 4,400,196 and also Proc. EWRS Symp. "Factors Affecting Herbicidal Activity and Selectivity", 227-232 (1988). Nonionic fatty alcohol polyglycol ethers are, for example, ($C_{10}$-$C_{18}$)—, preferably ($C_{10}$-$C_{14}$)-fatty alcohol polyglycol ethers (for example isotridecyl alcohol polyglycol ethers) which comprise, for example, 2-20, preferably 3-15, ethylene oxide units, for example those from the Genapol® X-series, such as Genapol® X-030, Genapol® X-060, Genapol® X-080 or Genapol® X-150 (all from Clariant).

The herbicidal action can also be enhanced by using vegetable oils. The term vegetable oils is to be understood as meaning oils of oleaginous plant species, such as soybean oil, rapeseed oil, corn oil, sunflower oil, cottonseed oil, linseed oil, coconut oil, palm oil, thistle oil or castor oil, in particular rapeseed oil, and also their transesterification products, for example alkyl esters, such as rapeseed oil methyl ester or rapeseed oil ethyl ester.

The vegetable oils are preferably esters of $C_{10}$-$C_{22}$-, preferably $C_{12}$-$C_{20}$-, fatty acids. The $C_{10}$-$C_{22}$-fatty acid esters are, for example, esters of unsaturated or saturated $C_{10}$-$C_{22}$-fatty acids, in particular those having an even number of carbon atoms, for example erucic acid, lauric acid, palmitic acid and in particular $C_{18}$-fatty acids, such as stearic acid, oleic acid, linoleic acid or linolenic acid.

Examples of $C_{10}$-$C_{22}$-fatty acid esters are esters obtained by reacting glycerol or glycol with the $C_{10}$-$C_{22}$-fatty acids contained, for example, in oils of oleaginous plant species, or $C_1$-$C_{20}$-alkyl-$C_{10}$-$C_{22}$-fatty acid esters which can be obtained, for example, by transesterification of the aforementioned glycerol- or glycol-$C_{10}$-$C_{22}$-fatty acid esters with $C_1$-$C_{20}$-alcohols (for example methanol, ethanol, propanol or butanol). The transesterification can be carried out by known methods as described, for example, in Römpp Chemie Lexikon, 9th edition, Volume 2, page 1343, Thieme Verlag Stuttgart.

Preferred $C_1$-$C_{20}$-alkyl-$C_{10}$-$C_{22}$-fatty acid esters are methyl esters, ethyl esters, propyl esters, butyl esters, 2-ethylhexyl esters and dodecyl esters. Preferred glycol- and glycerol-$C_{10}$-$C_{22}$-fatty acid esters are the uniform or mixed glycol esters and glycerol esters of $C_{10}$-$C_{22}$-fatty acids, in particular fatty acids having an even number of carbon atoms, for example erucic acid, lauric acid, palmitic acid and, in particular, $C_{18}$-fatty acids, such as stearic acid, oleic acid, linoleic acid or linolenic acid.

In the combinations according to the invention, the vegetable oils can be present, for example, in the form of commercially available oil-containing formulation additives, in particular those based on rapeseed oil, such as Hasten® (Victorian Chemical Company, Australia, hereinbelow referred to as Hasten, main ingredient: rapeseed oil ethyl ester), Actirob®B (Novance, France, hereinbelow referred to as ActirobB, main ingredient: rapeseed oil methyl ester), Rako-Binol® (Bayer AG, Germany, hereinbelow referred to as Rako-Binol, main ingredient: rapeseed oil), Renol® (Stefes, Germany, hereinbelow referred to as Renol, vegetable oil ingredient: rapeseed oil methyl ester) or Mero® (Bayer CropScience, Germany, hereinbelow referred to as Mero, main ingredient: rapeseed oil methyl ester).

For application, the formulations present in commercial form are, if appropriate, diluted in a customary manner, for example in the case of wettable powders, emulsifiable concentrates, dispersions and water-dispersible granules with water. Preparations in the form of dusts, granules for soil application or granules for broadcasting and sprayable solutions are usually not diluted with other inert substances prior to application.

The active compounds A) and B) can be applied jointly or separately to the plants, parts of the plants, seeds of the plants or the area on which the plants grow (for example the area under cultivation), preferably to the green plants and parts of the plants and, if desired, additionally to the area under cultivation. One possible use is the joint application of the active compounds in the form of tank mixes, where the optimally formulated concentrated formulations of the individual active compounds are, together, mixed in a tank with water, and the spray liquor obtained is applied.

A joint formulation of the active compounds of the herbicide/azole combination according to the invention has the advantage that it can be applied more easily since the quantities of the components are already adjusted to the correct ratio. Moreover, the additives in the formulation can be adjusted optimally to one another, whereas a tank mix of different formulations may result in unwanted combinations of additives.

A. General Formulation Examples a) A dust is obtained by mixing 10 parts by weight of an active compound/active compound mixture and 90 parts by weight of talc as inert substance and comminuting the mixture in a hammer mill.

b) A wettable powder which is readily dispersible in water is obtained by mixing 25 parts by weight of an active compound/active compound mixture, 64 parts by weight of kaolin-containing quartz as inert substance, 10 parts by weight of potassium lignosulfonate and 1 part by weight of sodium oleoylmethyltaurinate as wetting agent and dispersant, and grinding the mixture in a pinned-disk mill.

c) A dispersion concentrate which is readily dispersible in water is obtained by mixing 20 parts by weight of an active compound/active compound mixture with 6 parts by weight of alkylphenol polyglycol ether (Triton® X 207), 3 parts by weight of isotridecanol polyglycol ether (8 EO) and 71 parts by weight of paraffinic mineral oil (boiling range for example approximately 255 to 277° C.) and grinding the mixture in a ball mill to a fineness of below 5 microns.

d) An emulsifiable concentrate is obtained from 15 parts by weight of an active compound/active compound mixture, 75 parts by weight of cyclohexanone as solvent and 10 parts by weight of ethoxylated nonylphenol as emulsifier.

e) Water-dispersible granules are obtained by mixing
75 parts by weight of an active compound/active compound mixture,
10 parts by weight of calcium lignosulfonate,
5 parts by weight of sodium lauryl sulfate,
3 parts by weight of polyvinyl alcohol and
7 parts by weight of kaolin,
grinding the mixture in a pinned-disk mill, and granulating the powder in a fluidized bed by spraying on water as granulating liquid.

f) Water-dispersible granules are also obtained by homogenizing and precomminuting, in a colloid mill,
25 parts by weight of an active compound/active compound mixture,
5 parts by weight of sodium 2,2'-dinaphthylmethane-6,6'-disulfonate,
2 parts by weight of sodium oleoylmethyltaurinate,
1 part by weight of polyvinyl alcohol,
17 parts by weight of calcium carbonate and
50 parts by weight of water,
subsequently grinding the mixture in a bead mill and atomizing and drying the resulting suspension in a spray tower by means of a single-substance nozzle.

B. Biological Examples

Herbicidal Action

Greenhouse Trials

The seeds of typical harmful plants and of typical cereal plants were sown, allowed to emerge and grown under greenhouse conditions. Treatment with the compositions according to the invention was carried out after emergence of the harmful plants generally at the 2- to 4-leaf stage at various dosages using a water application rate of 300 l/ha (converted).

After the treatment (approx. 4 weeks after application), the herbicidal activity of the active compounds or active compound mixtures was scored visually by comparing the treated plots with untreated control plots. Damage and development of all above-ground parts of the plants was recorded. Scoring was done on a percentage scale (100% activity=all plants dead; 50% activity=50% of the plants and green plant parts dead; 0% activity=no discernible activity=like control plot).

The results are listed in the tables below, where the activity measured for the independent use of the active compounds A) and B) is stated in brackets and g of AS/ha means gram of active substance per hectare.

Example 1

| Active compound(S) | g of AS/ha | Alopecurus myosuroidis % activity | Lolium multiflorum % activity | Wheat % damage |
| --- | --- | --- | --- | --- |
| A)(A1.1)$^S$ | 10 | 83 | 30 | 25 |
| B) epoxiconazole | 125 | 0 | 0 | 0 |
|  | 250 | 0 | 0 | 0 |
| A) + B) | 10 + 125 | 96 (83 + 0) | 70 (30 + 0) | 15 (0 + 25) |
|  | 10 + 250 | 98 (83 + 0) | 70 (30 + 0) | 20 (0 + 25) |

(A1.1)$^S$ = mesosulfuron-methyl (A1.1) + mefenpyr-diethyl (S1 – 1) in a weight ratio of 1:3

The invention claimed is:

1. A herbicide azole combination comprising components (A) and (B),
wherein,
(A) comprises mesosulfuron-methyl (A2.1), and
(B) comprises epoxiconazole (B8),
wherein the components (A) and (B) are present in a synergistically effective amount.

2. The herbicide azole combination as claimed in claim 1, further comprising, as component (A), at least one herbicidally active compound selected from the group consisting of iodosulfuron-methyl (A1.1), iodosulfuron-methyl-sodium (A1.2), mesosulfuron-methyl-sodium (A2.2), flucarbazone (A4.1), flucarbazone-sodium (A4.2), propoxycarbazone (A5.1) and propoxycarbazone-sodium (A5.2).

3. The herbicide azole combination as claimed in claim 1, further comprising, as component (B), at least one agrochemically active compound selected from the group consisting of cyproconazole (B3), fluquinconazole (B11), propiconazole (B20), prothioconazole (B21), tebuconazole (B24) and myclobutanil (B35).

4. The herbicide azole combination as claimed in claim 1, further comprising at least one further component selected from the group consisting of agrochemically active compounds of a different type and additives and formulation auxiliaries customary in crop protection.

5. A method for controlling harmful plants comprising applying the components of the herbicide azole combination, as claimed in claim 1, jointly or separately to a plant, a plant part, a plant seed and/or an area on which a plant grows.

6. The method as claimed in claim 5 for the selective control of harmful plants in plant crops.

7. The method as claimed in claim 6 for the control of harmful plants in monocotyledonous plant crops.

8. The method as claimed in claim 6 in which the plant crops are genetically modified and/or have been obtained by mutation or selection.

9. The herbicide azole combination of claim 1 that is adapted for controlling harmful plants.

10. A method of claim 7, wherein the plant crops are genetically modified and/or have been obtained by mutation or selection.

11. The combination as claimed of claim 2, further comprising, as component (B) at least one agrochemically active compound selected from the group consisting of cyproconа- zole (B3), fluquinconazole (B11), propiconazole (B20), prothioconazole (B21), tebuconazole (B24) and myclobutanil (B35).

12. The combination of claim 2, further comprising at least one, further component selected from the group consisting of agrochemically active compounds of a different type and additives and formulation auxiliaries customary in crop protection.

13. The combination of claim 3, further comprising at least one, further component selected from the group consisting of agrochemically active compounds of a different type and additives and formulation auxiliaries customary in crop protection.

14. The method of claim 5, wherein the application rate of component (A) is in a range of 1 g to 50 g of active ingredient per hectare, and wherein the application rate of component (B) is in a range of 0.01 kg to 0.25 kg of active ingredient per hectare.

15. The method of claim 5, wherein the application rate ratio of component (A) to component (B) is in a range 1:15 to 2:1.

16. The combination of claim 1, further comprising mefenpyr-diethyl.

17. The method of claim 5, wherein component (A) and component (B) are applied jointly.

18. The method of claim 5, wherein component (A) and component (B) are applied separately.

19. The method of claim 5, wherein the application rate ratio of component (A) to component (B) is in a range 1:50 to 2:1.

20. The method of claim 5, wherein the application rate ratio of component (A) to component (B) is in a range 1:25 to 2:1.

* * * * *